US010632243B2

United States Patent
Rohde et al.

(10) Patent No.: US 10,632,243 B2
(45) Date of Patent: Apr. 28, 2020

(54) SYSTEM AND METHOD FOR PERFORMING ALTERNATIVE AND SEQUENTIAL BLOOD AND PERITONEAL DIALYSIS MODALITIES

(71) Applicants: Baxter International Inc., Deerfield, IL (US); Baxter Healthcare S.A., Glattpark (Opfikon) (CH)

(72) Inventors: Justin Belanger Rohde, Des Plaines, IL (US); Marc Steven Minkus, Bannockburn, IL (US)

(73) Assignees: Baxter International Inc., Deerfield, IL (US); Baxter Healthcare SA, Glattpark (Opfikon) (CH)

(*) Notice: Subject to any disclaimer, the term of this patent is extended or adjusted under 35 U.S.C. 154(b) by 291 days.

(21) Appl. No.: 15/259,840

(22) Filed: Sep. 8, 2016

(65) Prior Publication Data

US 2016/0375189 A1     Dec. 29, 2016

Related U.S. Application Data

(63) Continuation of application No. 13/828,731, filed on Mar. 14, 2013, now Pat. No. 9,440,017.

(51) Int. Cl.
*A61M 1/14*     (2006.01)
*A61M 1/28*     (2006.01)
(Continued)

(52) U.S. Cl.
CPC .............. *A61M 1/281* (2014.02); *A61M 1/14* (2013.01); *A61M 1/16* (2013.01); *A61M 1/1605* (2014.02);
(Continued)

(58) Field of Classification Search
CPC ...... A61M 2205/33; A61M 1/28; A61M 1/14; A61M 1/287
See application file for complete search history.

(56) References Cited

U.S. PATENT DOCUMENTS

| 3,707,967 A | 1/1973 | Kitrilakis et al. |
| 3,712,474 A | 1/1973 | Martinez |

(Continued)

FOREIGN PATENT DOCUMENTS

| CA | 2905258 | 3/2019 |
| EP | 0694312 | 1/1996 |

(Continued)

OTHER PUBLICATIONS

Marcus Manns et al., "The acu-men™: A new device for continuous renal replacement therapy in acute renal failure," Kidney Int'l., 1998, 54:1, 268-274.

(Continued)

*Primary Examiner* — Kai H Weng
(74) *Attorney, Agent, or Firm* — K&L Gates LLP

(57) ABSTRACT

A dialysis system includes at least one source of fluid for dialysis, a fluid line in fluid communication with the at least one source of fluid, at least one pump positioned and arranged to pump fluid from the at least one source of fluid through the fluid line, a first patient connector configured to be removably placed in fluid communication with the fluid line to allow a blood treatment to be performed using the at least one source of fluid, and a second patient connector configured to be removably placed in fluid communication with the fluid line to allow a peritoneal dialysis treatment to be performed using the at least one source of fluid.

21 Claims, 8 Drawing Sheets

(51) Int. Cl.
  *A61M 1/16* (2006.01)
  *A61M 1/36* (2006.01)
  *A61M 1/34* (2006.01)
(52) U.S. Cl.
  CPC .......... *A61M 1/167* (2014.02); *A61M 1/1656* (2013.01); *A61M 1/1666* (2014.02); *A61M 1/1668* (2014.02); *A61M 1/28* (2013.01); *A61M 1/284* (2014.02); *A61M 1/287* (2013.01); *A61M 1/288* (2014.02); *A61M 1/34* (2013.01); *A61M 1/3406* (2014.02); *A61M 1/36* (2013.01); *A61M 1/3655* (2013.01); *A61M 2205/15* (2013.01); *A61M 2205/33* (2013.01); *A61M 2205/3303* (2013.01); *A61M 2205/3331* (2013.01); *A61M 2205/3368* (2013.01); *A61M 2205/502* (2013.01)

(56) References Cited

U.S. PATENT DOCUMENTS

| | | |
|---|---|---|
| 3,712,475 A | 1/1973 | Martinez |
| 3,734,298 A | 5/1973 | Riede et al. |
| 3,791,767 A | 2/1974 | Schill |
| 3,830,234 A | 8/1974 | Kopp |
| 3,837,496 A | 9/1974 | Hagstrom et al. |
| 3,841,491 A | 10/1974 | Hagstrom et al. |
| 3,857,785 A | 12/1974 | Martinez |
| RE29,346 E | 8/1977 | Kopp |
| 4,085,046 A | 4/1978 | Saporito, Jr. |
| 4,093,545 A | 6/1978 | Cullis |
| 4,094,775 A | 6/1978 | Mueller |
| 4,122,010 A | 10/1978 | Riede et al. |
| 4,140,633 A | 2/1979 | Goldhaber |
| 4,141,834 A | 2/1979 | Bellotti et al. |
| 4,142,974 A | 3/1979 | Bellotti et al. |
| 4,202,764 A | 5/1980 | Afflerbaugh et al. |
| 4,234,428 A | 11/1980 | Schnell |
| 4,235,231 A | 11/1980 | Schindler et al. |
| 4,240,408 A | 12/1980 | Schael |
| 4,348,280 A | 9/1982 | George et al. |
| 4,353,368 A | 10/1982 | Slovak et al. |
| 4,443,333 A | 4/1984 | Mahurkar |
| 4,468,329 A | 8/1984 | Shaldon et al. |
| 4,479,762 A | 10/1984 | Bilstad et al. |
| 4,486,189 A | 12/1984 | Troutner et al. |
| 4,490,134 A | 12/1984 | Troutner |
| 4,514,295 A | 4/1985 | Mathieu et al. |
| 4,552,552 A | 11/1985 | Polaschegg |
| 4,560,472 A | 12/1985 | Granzow et al. |
| 4,585,436 A | 4/1986 | Davis et al. |
| 4,586,920 A | 5/1986 | Peabody |
| 4,596,550 A | 6/1986 | Troutner |
| 4,610,665 A | 9/1986 | Matsumoto et al. |
| 4,610,781 A | 9/1986 | Bilstad et al. |
| 4,618,343 A | 10/1986 | Polaschegg |
| 4,655,762 A | 4/1987 | Rogers |
| 4,683,053 A | 7/1987 | Polaschegg |
| 4,711,715 A | 12/1987 | Polaschegg |
| 4,718,890 A | 1/1988 | Peabody |
| 4,726,381 A | 2/1988 | Jones |
| 4,747,822 A | 5/1988 | Peabody |
| 4,765,339 A | 8/1988 | Jones |
| 4,828,543 A | 5/1989 | Weiss et al. |
| 4,935,125 A | 6/1990 | Era et al. |
| 4,940,455 A | 7/1990 | Guinn |
| 4,997,570 A | 3/1991 | Polaschegg |
| 5,004,459 A | 4/1991 | Peabody |
| 5,024,756 A | 6/1991 | Sternby |
| 5,141,493 A | 8/1992 | Jacobsen et al. |
| 5,173,125 A | 12/1992 | Felding |
| 5,211,913 A | 5/1993 | Hagiwara et al. |
| 5,334,139 A | 8/1994 | Jeppsson et al. |
| 5,342,527 A | 8/1994 | Chevallet et al. |
| 5,350,357 A | 9/1994 | Kamen et al. |
| 5,421,208 A | 6/1995 | Packard et al. |
| 5,421,823 A | 6/1995 | Packard et al. |
| 5,429,802 A | 7/1995 | Hagiwara et al. |
| 5,431,626 A | 7/1995 | Bryant et al. |
| 5,438,510 A | 8/1995 | Bryant et al. |
| 5,470,483 A | 11/1995 | Bene et al. |
| 5,474,683 A | 12/1995 | Bryant et al. |
| 5,498,338 A | 3/1996 | Kruger et al. |
| 5,507,723 A | 4/1996 | Keshaviah |
| 5,522,998 A | 6/1996 | Polaschegg |
| 5,529,685 A | 6/1996 | Irie et al. |
| 5,542,919 A | 8/1996 | Simon et al. |
| 5,582,794 A | 12/1996 | Hagiwara et al. |
| 5,620,604 A | 4/1997 | Stone |
| 5,628,908 A | 5/1997 | Kamen et al. |
| 5,641,144 A | 6/1997 | Hendrickson et al. |
| 5,685,988 A | 11/1997 | Malchesky |
| 5,702,597 A | 12/1997 | Chevallet et al. |
| 5,722,947 A | 3/1998 | Jeppsson et al. |
| 5,725,776 A | 3/1998 | Kenley et al. |
| 5,755,968 A | 5/1998 | Stone |
| 5,782,796 A | 7/1998 | Din et al. |
| 5,843,474 A | 12/1998 | Williams |
| 5,938,634 A | 8/1999 | Packard |
| 5,984,891 A | 11/1999 | Keilman et al. |
| 5,989,423 A | 11/1999 | Kamen et al. |
| 6,039,877 A | 3/2000 | Chevallet et al. |
| 6,074,359 A | 6/2000 | Keshaviah et al. |
| 6,117,122 A | 9/2000 | Din et al. |
| 6,168,578 B1 | 1/2001 | Diamond |
| 6,196,992 B1 | 3/2001 | Keilman et al. |
| 6,254,567 B1 | 7/2001 | Treu et al. |
| 6,280,634 B1 | 8/2001 | Shah et al. |
| 6,284,131 B1 | 9/2001 | Hogard et al. |
| 6,458,275 B1 | 10/2002 | Shukla et al. |
| 6,488,647 B1 | 12/2002 | Miura et al. |
| 6,491,658 B1 | 12/2002 | Miura et al. |
| 6,558,347 B1 | 5/2003 | Jhuboo et al. |
| 6,595,944 B2 | 7/2003 | Balschat et al. |
| 6,595,948 B2 | 7/2003 | Suzuki et al. |
| 6,638,477 B1 | 10/2003 | Treu et al. |
| 6,645,166 B2 | 11/2003 | Scheunert et al. |
| 6,673,314 B1 | 1/2004 | Burbank et al. |
| 6,676,621 B1 | 1/2004 | Menninger |
| 6,758,975 B2 | 7/2004 | Peabody et al. |
| 6,775,577 B2 | 8/2004 | Crnkovich et al. |
| 6,830,553 B1 | 12/2004 | Burbank et al. |
| 6,868,309 B1 | 3/2005 | Begelman |
| 6,955,655 B2 | 10/2005 | Bumank et al. |
| 6,979,309 B2 | 12/2005 | Burbank et al. |
| 7,004,924 B1 | 2/2006 | Brugger et al. |
| 7,029,456 B2 | 4/2006 | Ware et al. |
| 7,112,273 B2 | 9/2006 | Weigel et al. |
| 7,115,107 B2 | 10/2006 | Delnevo et al. |
| 7,131,956 B1 | 11/2006 | Pirazzoli et al. |
| 7,153,286 B2 | 12/2006 | Busby et al. |
| 7,208,092 B2 | 4/2007 | Micheli |
| 7,214,312 B2 | 5/2007 | Brugger et al. |
| 7,223,336 B2 | 5/2007 | Tonelli et al. |
| 7,223,338 B2 | 5/2007 | Duchamp et al. |
| 7,226,538 B2 | 6/2007 | Brugger et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,264,607 B2 | 9/2007 | Caleffi |
| 7,264,730 B2 | 9/2007 | Connell et al. |
| 7,267,658 B2 | 9/2007 | Treu et al. |
| 7,291,123 B2 | 11/2007 | Baraldi et al. |
| 7,291,269 B2 | 11/2007 | Chevallet et al. |
| 7,300,413 B2 | 11/2007 | Burbank et al. |
| 7,303,680 B2 | 12/2007 | Connell et al. |
| 7,314,554 B2 | 1/2008 | Delnevo et al. |
| 7,316,662 B2 | 1/2008 | Delnevo et al. |
| 7,318,892 B2 | 1/2008 | Connell et al. |
| 2003/0135152 A1 | 7/2003 | Kollar et al. |
| 2004/0182787 A1* | 9/2004 | Chevallet .............. A61L 2/0011 210/646 |
| 2005/0006296 A1 | 1/2005 | Sullivan et al. |
| 2005/0082210 A1 | 4/2005 | Favre |

(56) References Cited

U.S. PATENT DOCUMENTS

| | | |
|---|---|---|
| 2005/0131332 A1 | 6/2005 | Kelly et al. |
| 2005/0173344 A1 | 8/2005 | Bowman et al. |
| 2009/0008306 A1 | 1/2009 | Cicchello et al. |
| 2009/0101550 A1 | 4/2009 | Muller et al. |
| 2016/0375189 A1 | 12/2016 | Rohde et al. |

FOREIGN PATENT DOCUMENTS

| | | |
|---|---|---|
| EP | 1314442 | 5/2003 |
| GB | 2052303 | 1/1981 |
| WO | WO2006/011009 | 2/2006 |

OTHER PUBLICATIONS

Feng GH et al., "Combination of Hemofiltration and Peritoneal Dialysis in the Treatment of Severe Acute Pancreatitis", Chin J. Surg, Mar. 2004, vol. 42, No. 5, pp. 272-275.

Fukui Hara et al., "Review of Combination of Peritoneal Dialysis and Hemodialysis as a Modality of Treatment for Endstage Renal Disease", Therapeutic Apheresis and Dialysis, Aug. 2004, vol. 8(1), pp. 56-61.

Tadashi Tomo et al., "The Effect of Peritoneal Rest in Combination Therapy of Peritoneal Dialysis and Hemodialysis: Using the Cultured Human Peritoneal Mesothelial Cell Mode", The Japanese Society for Artificial Organs, Mar. 2005, vol. 8, pp. 125-129.

PCT International Search Report for Application No. PCT/US2008/068947 dated Apr. 16, 2009. 6 Pages.

PCT Written Opinion of the International Searching Authority for Application No. PCT/US20081068947 dated Apr. 16, 2009. 8 Pages.

International Search Report corresponding to related International Patent Application No. PCT/US2014/022659 dated Sep. 4, 2014.

International Written Opinion corresponding to related International Patent Application No. PCT/US2014/022659 dated Sep. 4, 2014.

Office Action issued in related Mexican Patent Application No. MX/a/2015/012582 dated Jul. 30, 2018. 6 pages.

Examination Report issued in corresponding Australian Patent Application No. 2014241074 dated Jul. 12, 2017. 5 pages.

Office Action issued in related German Patent Application No. 112014001324.2 dated May 17, 2017. 11 pages.

Office Action issued in related Australian Patent Application No. 2018201715 dated Dec. 6, 2018—5 pages.

Office Action issued in related Canadian Patent Application No. 3,008,435 dated Mar. 21, 2019—4 pages.

\* cited by examiner

SYSTEM AND METHOD FOR PERFORMING ALTERNATIVE AND SEQUENTIAL BLOOD AND PERITONEAL DIALYSIS MODALITIES

PRIORITY CLAIM

This application claims priority to and the benefit as a continuation application of U.S. patent application Ser. No. 13/828,731, entitled, "System and Method for Performing Alternative and Sequential Blood and Peritoneal Dialysis Modalities", filed Mar. 14, 2013, now U.S. Pat. No. 9,440,017, the entire contents of which is hereby incorporated by reference and relied upon.

CROSS-REFERENCE TO RELATED APPLICATION

This application is related by subject matter to U.S. patent application Ser. No. 11/773,634, entitled, "Extracorporeal Dialysis Ready Peritoneal Dialysis Machine", filed Jul. 5, 2007, now U.S. Pat. No. 8,512,553, and assigned to the assignee of the present application, the entire contents of which are hereby incorporated by reference and relied upon.

BACKGROUND

The examples discussed below relate generally to medical fluid delivery. More particularly, the examples disclose systems, methods and apparatuses for the control of fluid flow in kidney failure treatment systems.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 80 to 120 liters, is consumed during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting more than an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during dialysate. A "last fill" sometimes occurs at the end of APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

It is known with PD therapy that the diffusive properties of the peritoneum degrade over time due at least in part to chronic exposure to glucose. While research has been done to find an alternative osmotic agent, glucose remains the industry standard. Accordingly, a need exists for an improved PD therapy, which addresses the degradation of the effectiveness of the diffusive properties of the peritoneum over time.

SUMMARY

The examples below describe systems that provide an improved dialysis treatment. The systems address the degradation of clearance effectiveness of PD due to the chronic exposure of the peritoneum to glucose. In one preferred implementation of the systems described below, the systems are tailored to be used by the patient at home. It should be appreciated however that the machines are not limited to at home use and can instead be adapted for in-center or hospital use.

The systems in general provide an opportunity to the patient to alternate between peritoneal dialysis ("PD") and hemodialysis ("HD"). Alternating therapies provides two primary advantages, namely, preserving maximum residual renal function in PD and obtaining maximum urea clearance through HD. The systems provide "peritoneal rest" by enabling patients to perform HD over given intervals of time. Preliminary studies ([1]: Tomo T. et al J Artif Organs, 2005; 8(2): 125-9; [2] Zareie M., et al, *Nephrol Dial Transplant*, 2005 January; 20(1): 189-93; [3] Rodriquez A., *Advanced Peritoneal Dialysis*, 2002; 18:7880) indicate that "peritoneal rest" after one or more PD treatment allows the peritoneum to heal at least to some degree prior to the next exposure to glucose.

Disclosed below are three primary embodiments, namely, HD in combination with online batch PD, HD in combination with online continuous flow peritoneal dialysis ("CFPD"), and HD in combination with a simplified or bagged dialysate batch PD. In each of the three combinations, the HD therapy is the same, which is in one embodiment performed by making HD dialysate online and delivering the dialysate to and across the dialyzer to drain, while a blood pump pumps blood from a patient, to a dialyzer, cleaning the blood, and from the dialyzer, back to the patient.

In combination with the HD therapy, the first, online batch PD therapy swaps out the concentrates used to make HD dialysate with a PD dialysate concentrate and possibly a chemical disinfectant. The HD system hot water disinfects all blood and dialysate lines after a treatment in one embodiment. A subsequent PD treatment may also require that a chemical disinfectant be used alternatively or additionally with the hot water disinfection due to the fact that PD dialysate is delivered directly to the patient, heightening the need to high purity or sterility.

The online batch PD treatment primes the entire system with PD dialysate, after which a PD connection set 100 is connected to the primed and reused arterial and venous lines. The PD connection set is itself primed via pumping or gravity, after which the PD connection set is placed in fluid communication with the patient's transfer set. Batch PD dialysis is then performed with multiple fill, dwell and drain (full or tidal drains) cycles. Each drain cycle removes an amount of ultrafiltrate ("UF") absorbed via an osmotic gradient provided by the PD dialysate. If needed, an initial drain can be performed to remove a PD last fill from a patient's previous PD treatment.

In combination with the HD therapy, the second, CFPD therapy also swaps out the concentrates used to make HD dialysate with a PD dialysate concentrate and possibly the chemical disinfectant. The CFPD therapy can prime all lines the same as with the online batch PD treatment.

One primary difference between online batch PD and CFPD is that the CFPD connection set is a dual lumen connection set, while the online batch PD connection set can be a single lumen connection set that Y's or T's to connect to both the arterial and venous lines. The dual lumen CFPD connection set enables PD dialysate to be delivered to and removed from the patient's peritoneum simultaneously.

Another primary difference between CFPD and batch online PD is that CFPD flows PD dialysate continuously across the outsides of the dialyzer membranes to drain, while batch online PD pushes PD dialysate across the dialyzer membranes, into the PD patient circuit, into the patient for batch filling, and then stops. CFPD flows PD dialysate continuously on both sides of the dialyzer membranes in a manner similar to HD. The PD dialysate on the outsides of the dialyzer membranes osmotically cleans the PD dialysate on the insides of the dialyzer membranes, so that the PD dialysate delivered to the patient is continuously freshened. Again, the PD dialysate on the outside of the dialyzer membranes, which osmotically pulls patient waste products from the PD dialysate on the insides of the dialyzer membranes, is delivered to drain in one embodiment.

In combination with the HD therapy, the third, bagged dialysate batch PD therapy does not make dialysate online. Instead, a source of PD dialysate, such as a bag or container, is used. A single line patient connection set is used instead of the "Y" or "T" patient connection set used with online batch PD. The HD blood pump is used to pull PD dialysate from the source and push the PD dialysate through the dialyzer, the venous line and the single line patient connection set for priming, and then to the patient once priming is completed.

After a specified dwell period, the used dialysate or from-dialyzer dialysate pump is used to pull spent dialysate from the patient, across the dialyzer membranes, to drain. A new fill cycle can then be commenced. If the container is a single fill container, which is expired after the first fill, the blood pump can alternatively be used to drain the patient and push the effluent dialysate back to the source.

Multiple pneumatic configurations for pumping at higher pressures (positive and negative) for HD and at lower pressures (positive and negative) for PD are disclosed. Providing multiple pneumatic storage tanks with selective valving and/or providing electrically variable pressure regulators are examples discussed in detail below for providing higher pressures on HD therapy days and lower pressures on PD therapy days.

An alternative electrically controlled configuration is also disclosed. The pumps, and valves of the present disclosure are not limited to pneumatic pumps and valves. Peristaltic pumps operating with volumetric metering devices and solenoid pinch clamps, as disclosed below, may be used alternatively.

It is an advantage of the present disclosure to provide combination hemodialysis and peritoneal dialysis systems that can provide alternative therapies to the same patient on different days.

Another advantage of the present disclosure is to provide a single structure yielding multiple systems for automatically performing different modalities of dialysis as desired or prescribed.

A further advantage of the present disclosure is to provide a single structure that can pump at different pressures for different treatment modalities or therapies.

It is still another advantage of the patient disclosure to provide systems and methods that reuse the same (or largely the same) disposables for different therapies or treatment modalities.

It is yet another advantage of the patient disclosure to provide online systems and methods that can be used for multiple therapies or treatment modalities.

Additional features and advantages are described herein, and will be apparent from, the following Detailed Description and the figures.

DETAILED DESCRIPTION

HD and Batch PD

Figure 1:
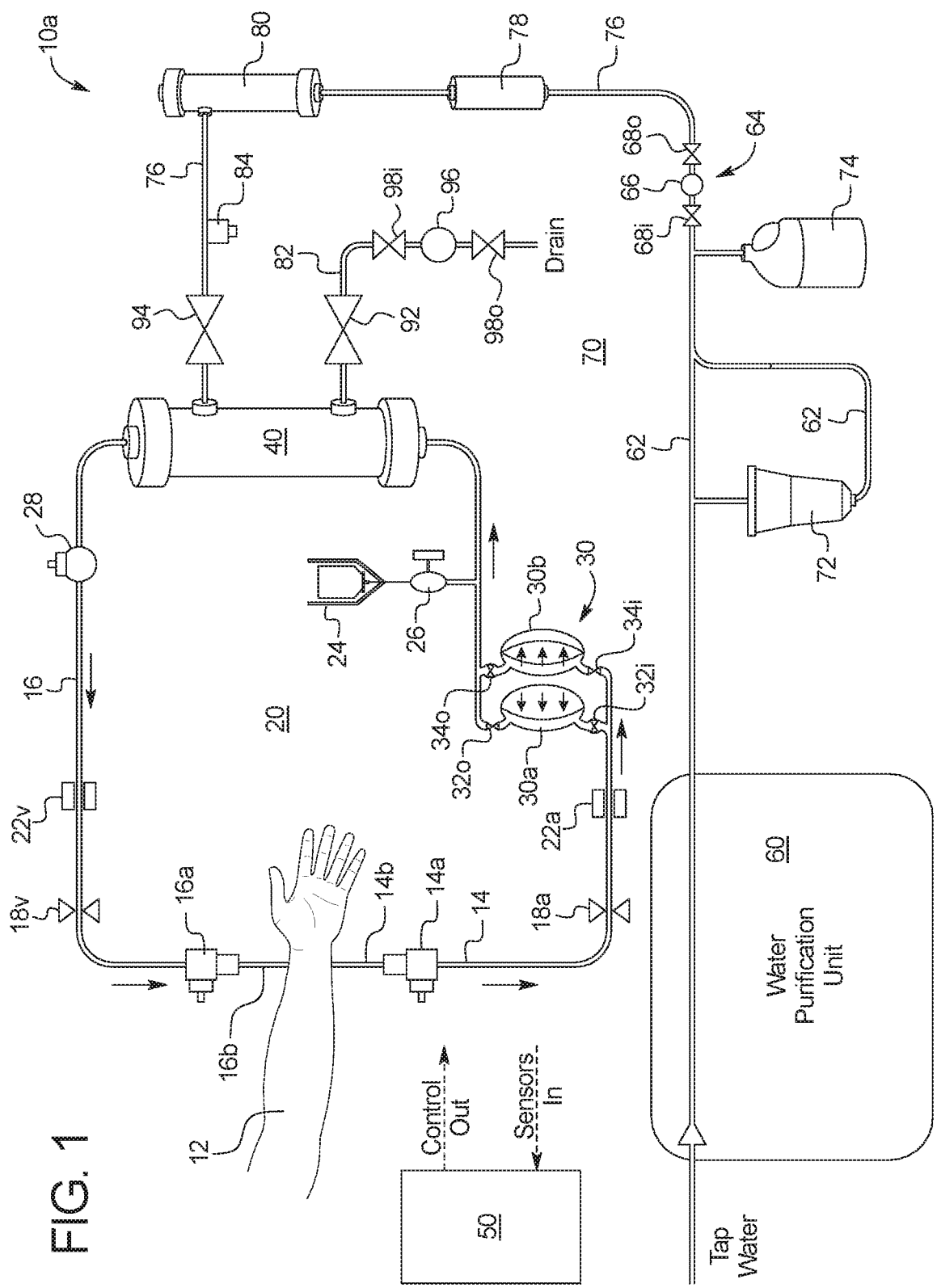
FIG. 1 is a schematic view of one embodiment of a hemodialysis ("HD") system of the present disclosure.

Referring now to the drawings and in particular to FIG. 1, one embodiment for a combined PD/HD system is illustrated by system 10a. FIG. 1 is a simplified version of a hemodialysis ("HD") system. System 10a and any of the systems discussed here can include any of the structure and functionality described in U.S. Publication No. 2008/0216898, entitled, "Cassette System Integrated Apparatus", filed Feb. 27, 2008, and in U.S. Publication No. 2013/0037480, entitled, "Hemodialysis Systems And Methods", filed Aug. 8, 2012, the entire contents of each of which (referred to herein as the "referenced publications") are hereby incorporated by reference and relied upon. Generally, the systems shown herein include a very simplified version of the dialysate or process fluid delivery circuit. The blood circuits are also simplified but not to the degree that the dialysate circuit is simplified. It should be appreciated that the circuits have been simplified to make the description of the present disclosure easier, and that the systems if implemented would have additional structure and functionality, such as is found in the referenced publications listed above.

System 10a of FIG. 1 includes a blood circuit 20. Blood circuit 20 pulls blood from and returns blood to a patient 12. Blood is pulled from patient 12 via an arterial line 14, and is returned to the patient via a venous line 16. Arterial line 14 includes an arterial line connector 14a that connects to an arterial needle 14b, which is in blood draw flow communication with patient 12. Venous line 16 includes a venous line connector 16a that connects to a venous needle 16b, which is in blood return flow communication with the patient. Arterial and venous lines 14 and 16 also include line clamps 18a and 18v, which can be a spring-loaded, fail safe mechanical pinch clamps. Line clamps 18a and 18v are closed automatically in an emergency situation in one embodiment.

Arterial and venous lines 14 and 16 also include air or bubble detectors 22a and 22v, respectively, which can be ultrasonic air detectors. Air or bubble detectors 20a and 20v look for air in the arterial and venous lines 14 and 16, respectively. If air is detected by one of air detectors 22a and 22v, system 10a closes line clamps 18a and 18v, pauses the blood and dialysate pumps and provides instructions to the patient to clear the air so that treatment can resume.

A blood pump 30 is located in arterial line 14 in the illustrated embodiment. In the illustrated embodiment, blood pump 30 includes a first blood pump pod 30a and a second blood pump pod 30b. Blood pump pod 30a operates with an inlet valve 32i and an outlet valve 32o. Blood pump pod 30b operates with an inlet valve 34i and an outlet valve 34o. In an embodiment, blood pump pods 30a and 30b are each blood receptacles that include a hard outer shell, e.g., spherical, with a flexible diaphragm located within the shell, forming a diaphragm pump. Once side of each diaphragm receives blood, while the other side of each diaphragm is operated by negative and positive air pressure.

To operate blood pump pods 30a and 30b, taking pod 30a for example, inlet valve 32i is opened, while outlet valve 32o is closed, and while negative air pressure is applied to the diaphragm to draw blood into blood pump pod 30a. Conversely, inlet valve 32i is closed, while outlet valve 32o is opened, and while positive air pressure is applied to the diaphragm to push blood out of blood pump pod 30a. The same is done for blood pump pod 30b using inlet valve 34i and an outlet valve 34o. In one embodiment, blood pump pods 30a and 30b are operated sequentially so that while blood pump pods 30a is drawing in blood, blood pump pod 30b is pushing blood out, and vice versa. This allows blood flow to be relatively continuous through dialyzer 40.

A heparin vial 24 and heparin pump 26 are located between blood pump 30 and dialyzer 40 in the illustrated embodiment. Heparin pump 26 can be a pneumatic pump or a syringe pump (e.g., stepper motor driven syringe pump) as desired. Supplying heparin upstream of dialyzer 40 helps to prevent clotting of the dialyzer membranes.

A control unit 50 includes one or more processor and memory, receives air detection signals from air detectors 22a and 22v (and other sensors of system 10a, such as temperature sensors, blood leak detectors, conductivity sensors and pressure sensors), and controls components such as line clamps 18a and 18v, blood pump 30, heparin pump 26, and the dialysate pumps (described below).

Blood exiting dialyzer 40 flows through an airtrap 28. Airtrap 28 removes any air from the blood before the dialyzed blood is returned to patient 12 via venous line 16. Airtrap 28 can also have a pierceable septum that allows blood samples to be removed from blood circuit 20. Air that escapes airtrap 28 is sensed by venous air detector 22v. Control unit 50 receives the air sensed signal from venous air detector 22v and causes line clamps 18a and 18v to close and the user interface of system 10a (which in one embodiment is a tablet user interface) to display a clear air alarm screen. Arterial air detector 22a helps to detect whether arterial line connector 14a is properly connected to arterial needle 14b. At the end of prime, system 10a can pull blood from the patient into the arterial line 14 and venous line 16. At that time, venous air detector 22b can be used with control unit 50 detect whether venous line connector 16a is properly connected to venous needle 16b.

With hemodialysis system 10a of FIG. 1, dialysis fluid or dialysate is pumped along the outside of the membranes of dialyzer 40, while blood is pumped through the insides of the dialyzer membranes. Dialysis fluid or dialysate is prepared beginning with the purification of water by water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structure to purify tap water (e.g., remove pathogens and ions such as chlorine) so that the water is in one implementation below 0.03 endotoxin units/ml ("EU/ml") and below 0.1 colony forming units/ml ("CFU/ml"). Water purification unit 60 can be provided in a housing separate from the housing of the hemodialysis machine, which includes blood circuit 20 and a dialysate circuit 70.

Dialysate circuit 70 is again highly simplified in FIG. 1 to ease illustration and to better highlight blood circuit 20. Dialysate circuit 70 in actuality can include all of the relevant structure and functionality set forth in the referenced publications. Certain features of dialysate circuit 70 are illustrated in FIG. 1. In particular, dialysate circuit 70 includes a to-dialyzer dialysate pump 64. Pump 64 is in one embodiment configured the same a blood pump 30. Pump 64, like pump 30, includes a pair of pump pods, which again can be spherically configured. Only one pump pod 66 is illustrated, however, two pump pods are provided as with blood pump 30 in one embodiment. Inlet valve 68i and outlet valve 68o are sequenced with pump pod 66 to pull fluid into the pod (inlet valve 68i open, while outlet valve 68o closed) and to push fluid out of the pod (inlet valve 68i closed, while outlet valve 68o opened). The two pump pods, like with blood pump 30, are operated alternatingly so that one pump pod is filling with HD dialysate, while the other pump pod is expelling HD dialysate.

Pump 64 is a to-dialyzer dialysate pump. There is another dual pod pump 96, like pump 64, located in drain line 82 to push used dialysate to drain. There is a third pod pump (not illustrated) used to pump purified water through bicarbonate cartridge 72. There is a fourth pod pump (not illustrated) used to pump acid from container 74 into missing line 62.

The third and fourth pumps, the concentrate pumps, can be single pod pumps because continuous pumping is not as important in mixing line 62 because there is a buffering dialysate tank (not illustrated) between mixing line 62 and to-dialyzer dialysate pump 64 in one embodiment. A fifth pod pump (not illustrated) provided in drain line 82 is used to remove a known amount of ultrafiltration ("UF") when the HD therapy is provided.

Purified water from water purification unit 60 is pumped along a mixing line 62 though a bicarbonate cartridge 72. Acid from a container 74 is pumped along mixing line 62 into the bicarbonated water flowing from bicarbonate cartridge 72 to form an electrolytically and physiologically compatible dialysate solution. The pumps and temperature-compensated conductivity sensors used to properly mix the purified water with the bicarbonate and acid are not illustrated but are disclosed in detail in the referenced publications.

FIG. 1 also illustrates that dialysate is pumped along a fresh dialysate line 76, through a heater 78 and an ultrafilter 80, before reaching dialyzer 40 and dialyzing blood of patient 12, after which the used dialysate is pumped to drain via drain line 82. Heater 78 heats the dialysate to body temperature or about 37° C. Ultrafilter 80 further cleans and purifies the dialysate before reaching dialyzer 40, filtering bugs or contaminants introduced for example via bicarbonate cartridge 72 or acid container 74 from the dialysate.

Dialysate circuit 70 also includes a sample port 84 in the illustrated embodiment. Dialysate circuit 70 will further include a blood leak detector (not illustrated but used to detect if a dialyzer fiber is torn) and other components that are not illustrated, such as balance chambers, plural valves, and a dialysate holding tank, all illustrated and described in detail in the referenced applications.

Hemodialysis system 10a is an online, pass-through system that pumps dialysate through the dialyzer one time and then pumps the used dialysate to drain. Both blood circuit 20 and dialysate circuit 70 are hot water disinfected after each treatment, such that blood circuit 20 and dialysate circuit 70 can be reused. In one implementation, blood circuit 20 including dialyzer 40 are hot water disinfected and reused daily for about one month, while dialysate circuit 70 is hot water disinfected and reused for about six months. Prior to running the hot water disinfections, system 10a returns or rinses back the blood to patient 12. To do so, system 10a in one embodiment pushes dialysate across dialyzer 40 into blood circuit 20, which in turn pushes blood though both arterial and venous lines 14 and 16 back to patient 12. In an embodiment, system 10a knows how much dialysate to push into blood circuit 20 by knowing the volume of the blood circuit and counting known volume pump strokes until that volume is reached. Alternatively or additionally, a blood leak detector can be added to blood circuit 20 to look for a color change (from blood to clear) to know when to stop the blood rinseback process. In any case, at the end of the hemodialysis treatment, both circuits 20 and 70 are filled with dialysate.

Figure 2:
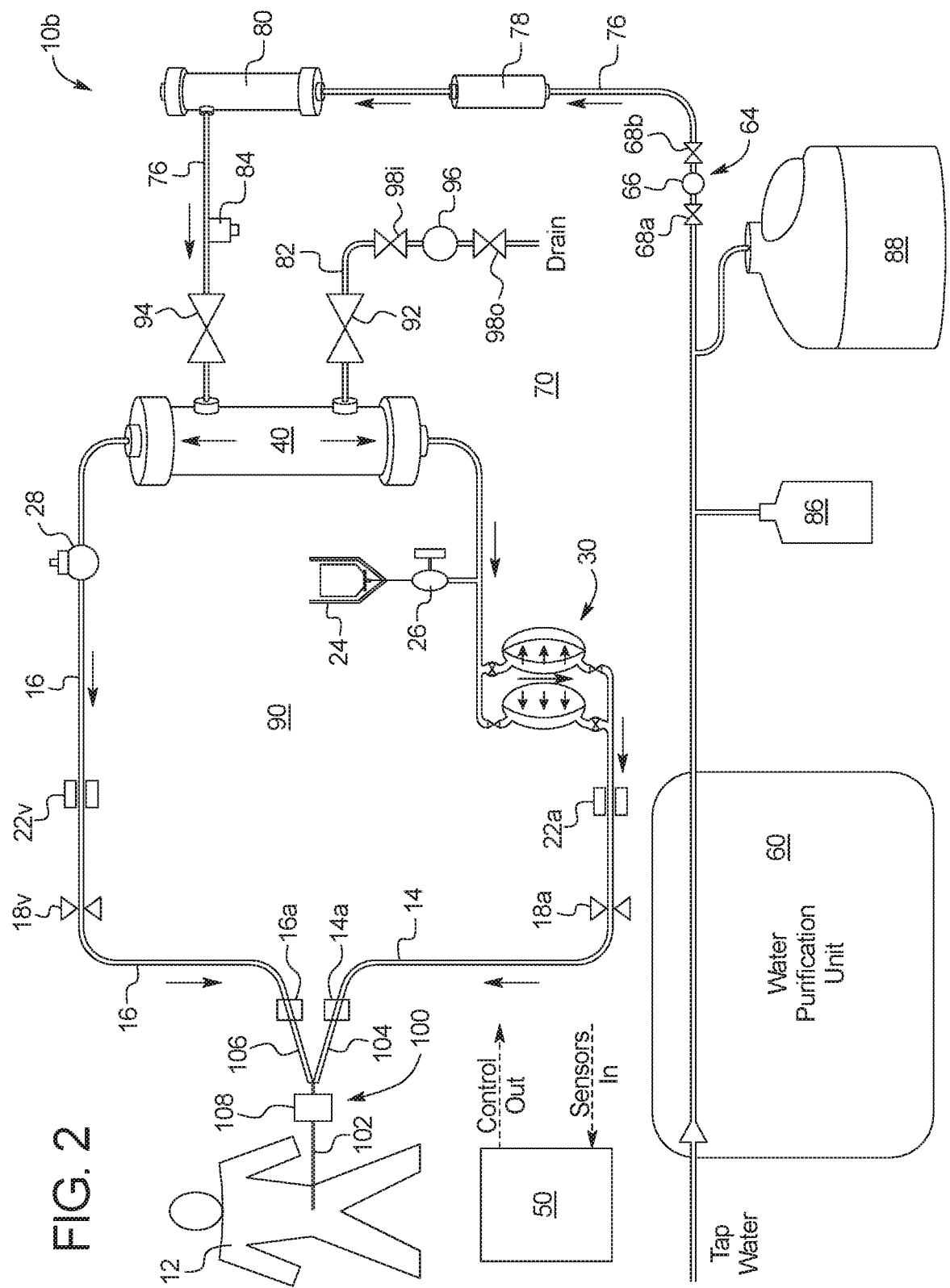
FIG. 2 is a schematic view of one embodiment of an online batch peritoneal dialysis ("PD") system in a filling mode, which can be used to perform an alternative PD therapy to the HD therapy of FIG. 1.
Figure 3:
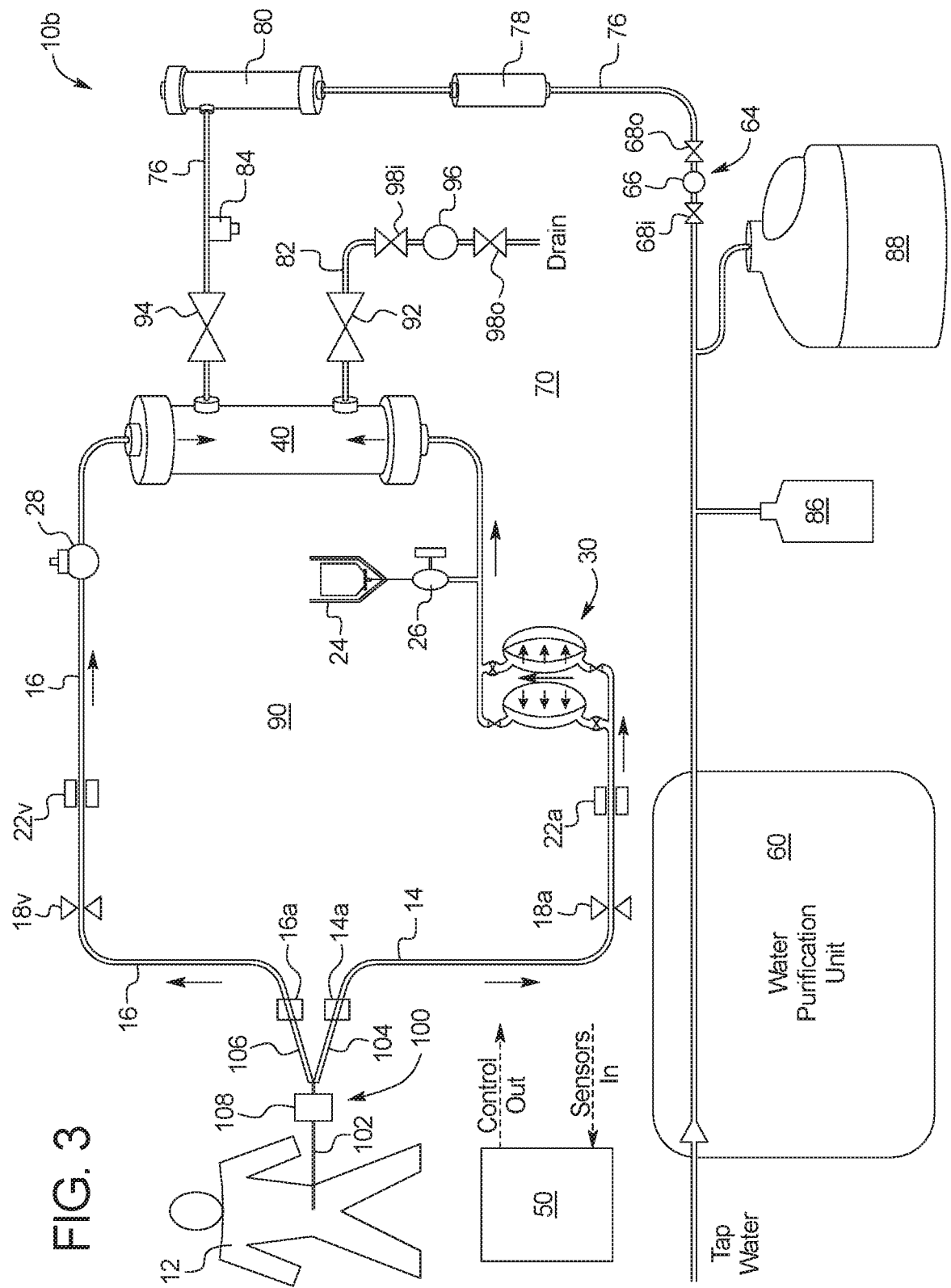
FIG. 3 is a schematic view of the online batch PD system of FIG. 2 in a draining mode.

Referring now to FIGS. 2 and 3, system 10b, using largely the same equipment as HD system 10a, is used instead to perform peritoneal dialysis. As discussed above in the SUMMARY, it has been reported that there are therapeutic benefits to alternating or mixing in peritoneal dialysis treatments into a hemodialysis regime and vice versa. System 10 (referring collectively to systems 10a and 10b) allows hemodialysis to be performed one day and the peritoneal dialysis to be performed the next day, and so on. Each element numbered the same in FIGS. 1 to 3 includes all of the structure, functionality and alternatives discussed herein, for example, as discussed in connection with FIG. 1. There are a few differences discussed next between the structure of hemodialysis system 10*a* in FIG. 1 and the structure of peritoneal dialysis system 10*b* as illustrated in FIGS. 2 and 3.

One primary difference is that bicarbonate cartridge 72 and acid container 74 of hemodialysis system 10*a* have been replaced by disinfect source 86 and peritoneal dialysis concentrate source 88 in FIGS. 2 and 3. Disinfect source 86 is used after the previous treatment, e.g., a hemodialysis treatment, during disinfection. Again, in one embodiment dialysis system 10 (referring to both systems 10*a* and 10*b*) heat disinfects blood circuit 20 and dialysate circuit 70 after treatment. If peritoneal dialysis is to be performed in the next treatment, then either before or after the hot water disinfection, system 10*b* operates a cycle in which a disinfectant is run through blood circuit 20 and dialysate circuit 70, e.g., over multiple passes, so that any bugs or contaminants left after the hot water disinfection has taken place are killed or removed to drain. This is done because instead of blood being pumped through blood circuit 20 in the next treatment, peritoneal dialysis fluid will be pumped through dialyzer 40, into arterial line 14 and venous line 16, and directly into patient 12. Accordingly, peritoneal dialysis system 10*b* must be as sterile as possible.

Suitable disinfectants for source 86 include renalin and peracetic acid, sold by under tradenames, such as Pericidin™, Actril™, Peristeril Plus™ and Puristeril 340™ and Minncare™. System 10*b* can in an embodiment proportion peracetic acid to a concentration of about 1% and deliver same to both circuits 20 and 70. Actril™ solution can be partially pre-diluted and then proportioned by system 10*b* to achieve the desired concentration. Another suitable disinfectant for source 86 is sodium hypochlorite (household bleach) provided at about five to six percent strength. Sodium hypochlorite can be used intermittently, e.g., once a week and, is particularly useful in removing organic deposits. System 10*b* can dilute sodium hypochlorite down to a 100 to 500 parts per million ("ppm"). One source of sodium hypochlorite is sold under the tradename Tuitol KF™ at 3.9% concentration. A further suitable disinfectant for source 86 is sold under the tradename Sporotal 100™, which includes sodium hypochlorite with potassium hydroxide and corrosion inhibitors, and which is particularly useful in removing biofilms.

System 10*b* in an embodiment rinses circuits 20 and 70 free of dialysis solution, introduces one of the disinfectants listed above, allows the disinfectant to dwell for a specified period of time, rinses the disinfectant out of circuits 20 and 70, and checks for residual disinfectant prior to use. The conductivity sensors (illustrated in the referenced publications) provided by systems 10*a* and 10*b* can be used to detect the presence or absence of disinfectant, e.g., for both bleach and peracetic acid, to ensure no disinfectant remains at the time of the next patient treatment. Alternatively or additionally, a residual disinfectant check can be performed by patient 12, nurse or caregiver using a test strip, e.g., a pH test strip, which can be specific to the disinfectant type. The chemical disinfectant can be performed before or during the hot water disinfect cycle or be performed after the hot water disinfection cycle and be followed by an additional hot water disinfections cycle.

Alternatively or additionally, during the hot water disinfection cycle, small amounts of anhydrous sodium carbonate powder (e.g., 13 grams) can be diluted by the proportioning or mixing circuit of systems 10*a* and 10*b* and used as a chemical during the heat disinfection cycle to remove organic deposits, fats and proteins.

Alternatively or additionally, during the hot water disinfection cycle, small amounts of citric acid anhydrate powder, e.g., 32 grams, can be diluted by the proportioning or mixing circuit of systems 10*a* and 10*b* as a chemical to disinfect and decalcify. Citric acid improves the disinfect efficiency because an 80° C. to 90° C. citric acid water solution will kill spore forming bacteria.

Alternatively or additionally, during the hot water disinfection cycle, citric acid liquid can be diluted by the proportioning or mixing circuit of systems 10*a* and 10*b* as a chemical to disinfect and decalcify. Again, citric acid liquid improves the disinfect efficiency because an 80° C. to 90° C. citric acid water solution will kill spore forming bacteria.

Alternatively or additionally, during the hot water disinfection cycle, hydroxy acetic acid and water under the tradename Diasteril™ can be used for chemical and heat disinfection similar to the citric acid heat treatment.

The heat disinfection cycle in an embodiment heats the water to 80° C. to 90° C., e.g., for fifteen minutes to one hour, and then cools circuits 20 and 70 with cool fresh water. In further alternative autoclave embodiment, heater 78 heats water to 120° C. and recirculates the hot water/steam, e.g., for fifteen minutes to one hour, through circuits 20 and 70 before cooling the circuits with cool fresh water.

In an embodiment, the pump used to pump purified water through bicarbonate cartridge 72 in FIG. 1 is used instead to pump disinfectant from source 86 in FIGS. 2 and 3. The pump used to pump acid from container 74 in FIG. 1 is used instead to pump peritoneal dialysis fluid concentrate from container 88. Disinfectant from source 86 can be provided in concentrated form and mixed with water from purification source 60 to provide a suitable volume of disinfection fluid, in a suitable concentration, to disinfect the entire system 10*b*.

In an embodiment, disinfection source 86 is provided in a volume sized to be used completely in one use. Control unit 50 knows the volume of disinfection source 86 and also the volume of fluid pumped by each stroke of the pod pump used to pump disinfectant from source 86. In this manner, control unit 50 can count full strokes of the disinfectant source pump and tally the amount of disinfectant pumped from the source until the full volume of disinfectant is removed from source 86. The disinfectant and purified water mixture is then circulated around and around system 10*b*. When chemical disinfection is completed, the disinfectant and purified water mixture is then pumped to drain via drain line 82, allowing system 10*b* to dry for the next treatment, which will be a peritoneal dialysis treatment.

Alternatively or in addition to chemical disinfection, peritoneal dialysis system 10*b* can use steam disinfection or ozone for sterilization. Ozone can be created online by subjecting oxygen to ultraviolet light. The ozone can then be drawn into purified water in mixing line 62, e.g., via a venture pump. Ozone tends not to store well under positive pressure.

Control unit 50 also knows the volume of fluid pumped by each stroke of the pod pump used to pump peritoneal dialysis fluid concentrate from container 88. In this manner, control unit 50 can count full strokes of the concentrate pump and tally the amount of concentrate pumped from container 88, so that the concentrate is mixed in the proper or desired proportion with purified water.

Hemodialysis dialysate is made in an embodiment using conductivity probes. When the dialysate reads the proper concentration, the dialysate is mixed properly. Peritoneal dialysis fluid is proportioned instead volumetrically in one embodiment using a known volume of purified water from unit 60 mixed with a known volume of concentrate, the volumes being known again by knowing the volume of each water pump stroke and each concentrate pump stroke. In an alternative embodiment, one or more sensor is used to servo the peritoneal dialysis fluid mixing, as is done with the hemodialysis fluid mixing. Sensors for servoing the peritoneal dialysis fluid mixing may include conductivity sensors and/or glucose sensors. Peritoneal dialysis concentrate for container 88 can include any one or more of dextrose, icodextrin, amino acids or bicarbonate. In an alternative embodiment, water purification unit 60 and concentrate container 88 are not used and bagged, premade peritoneal dialysis fluid is used instead to feed outer (meaning in fluid communication with the outsides of the dialyzer membranes) dialysate circuit 70.

Pump 64 pumps the online peritoneal dialysis fluid through heater 78 and ultrafilter 80 and into dialyzer 40 as illustrated in FIG. 2. Ultrafilter 80 and dialyzer 40 both serve to further purify the peritoneal dialysis ("PD") fluid before the fluid enters a PD patient circuit 90. PD patient circuit 90 in FIGS. 2 and 3 replaces blood circuit 20 in FIG. 1. Here, the hemodialysis needles 14*b* and 16*b* are replaced by a PD connection set 100. PD connection set 100 includes a patient line 102 that connects to the PD transfer set of patient 12. The patient's PD transfer set connects to a PD catheter dwelling inside patient 12. PD connection set 100 also includes a leg 104 that connects fluidly to arterial line connector 14*a*, and a leg 106 that connects fluidly to venous line connector 16*a*. PD connection set 100 further includes a small single use filter 108, such as a small ultrafilter, which acts as a final barrier against any bugs or contaminants entering patient 12.

Prior to connecting PD connection set 100 to arterial line connector 14*a* and venous line connector 16*a*, connectors 14*a* and 16*a* are connected together forming a closed loop that has been hot water and chemically disinfected, then dried. To-dialysate pump 64 pumps filtered PD fluid into PD patient circuit 90, where blood pump 30 circulates the PD fluid to push air through dialyzer 40 to drain via drain line 82 and open drain valve 92. When PD patient circuit 90 is fully primed, lines 14 and 16 are clamped, e.g., via manual pinch clamps such as Roberts™ clamps, connectors 14*a* and 16*a* are disconnected from each other and connected to PD connection set 100. Patient line 102 can have a removable hydrophobic tip or be placed at the same elevation as dialyzer 40, so that when lines 14 and 16 are unclamped, PD dialysate flows through PD connection set 100, pushing air out though patient line 102.

Patient line 102 is then connected to the patient's transfer set and drain valve 92 is closed. The patient can now be filled with PD dialysate as illustrated in FIG. 2. To do so in the illustrated embodiment, to-dialysate pump 64 pumps filtered PD fluid through venous line 16 to patient 12, while blood pump 30 pushes filtered PD fluid through arterial line 14 to patient 12. Alternatively, only one of to-dialysate pump 64 or blood pump 30 pushes filtered PD to patient 12. It does not matter which line 14 or 16 is used to deliver PD dialysate to patient 12. Further alternatively, PD connection set 100 may only include one of legs 104 and 106, which connects to one of connectors 14*a* and 16*a*, only. The other connector 14*a* or 16*a* is plugged or capped after priming.

Control unit 50 knows how much PD dialysate is delivered from primed PD patient circuit 90 to patient 12 again by counting known volume pump strokes of one or both of to-dialysate pump 64 or blood pump 30 in one embodiment.

Once the patient's peritoneum is filled with a prescribed fill volume, control unit 50 stops to-dialysate pump 64 and/or blood pump 30. The PD dialysate is then allowed to reside or dwell within the patient's peritoneum for a prescribed amount of time.

As illustrated in FIG. 3, when the prescribed dwell period has ended, control unit 50 opens drain valve 92 and closes delivery valve 94 in fresh dialysate line 76 to perform a drain phase. Valve 94 is open during the fill phase. To drain the patient, control unit 50 causes blood pump 30 and/or a from-dialyzer pump 96, operating with valves 98*i* and 98*o* as has been described herein, to pull the fill volume's worth of used PD dialysate and an expected amount of ultrafiltrate ("UF") from patient 12 and push same to drain via drain line 82. Control unit 50 again relies on pump stroke counting for volumetric accuracy to drain patient 12.

Control unit 50 then repeats the above-described fill, dwell and drain process. If patient 12 uses system 10*b* to perform peritoneal dialysis for multiple treatments in a row, the patient may have a full peritoneum from a last fill performed during a prior PD treatment when first connecting to PD patient circuit 90. If so, patient 12 can inform control unit 50 of same. Or, control unit 50 may already know that patient 12 needs to be drained and prompts the patient to do so. In either case, control unit 50 performs an initial drain through primed PD patient circuit 90 first before performing a first fill. In an alternative embodiment, patient 12 is prompted to perform a manual drain and enter the drain weight into control unit 50 before connecting to PD patient circuit 90.

HD and Continuous Flow PD

Figure 4:
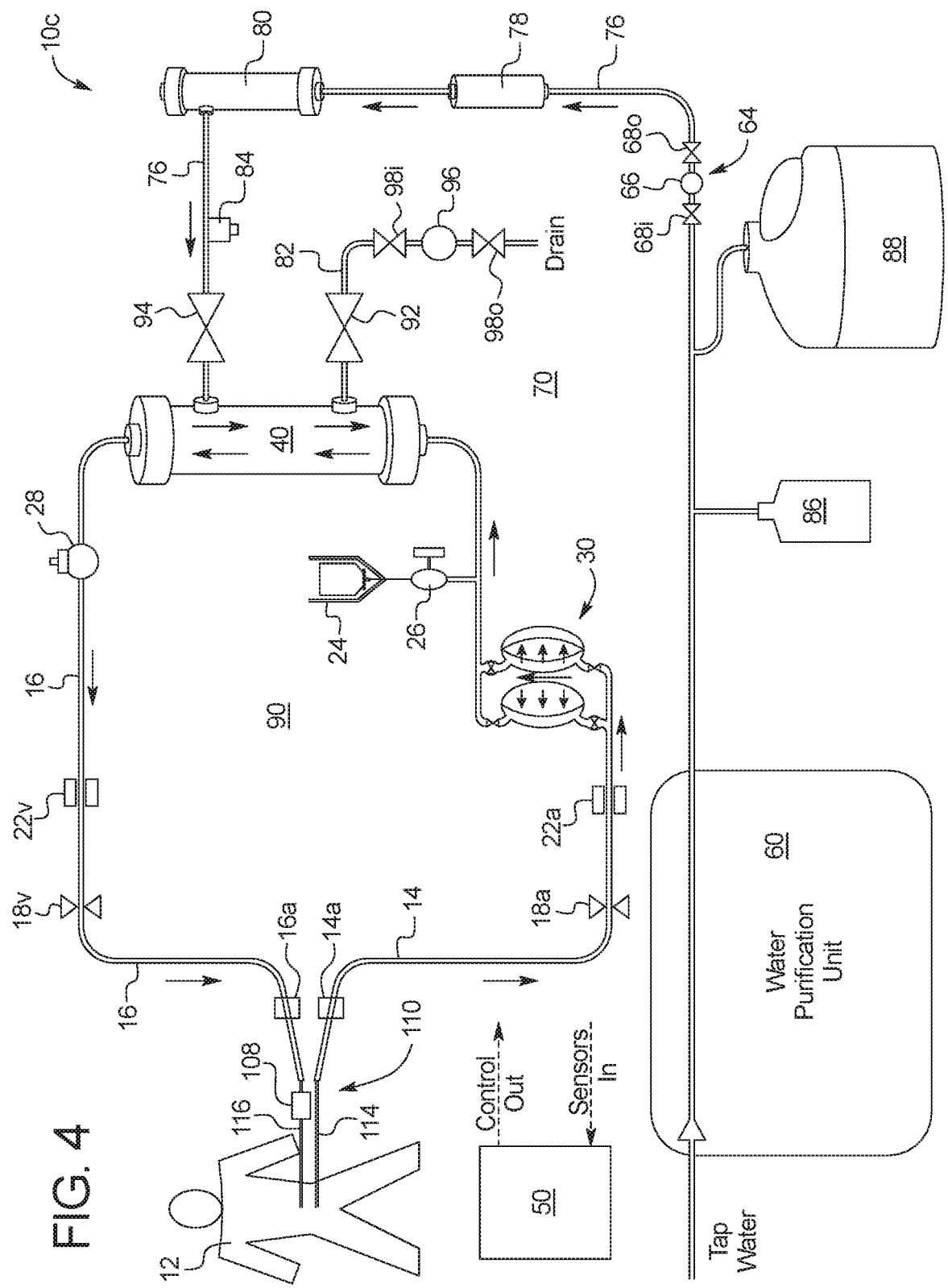
FIG. 4 is a schematic view of one embodiment of an online continuous flow peritoneal dialysis ("CFPD") system in a filling mode, which can be provided to perform an alternative therapy to the therapy of the HD system of FIG. 1.
Figure 5:
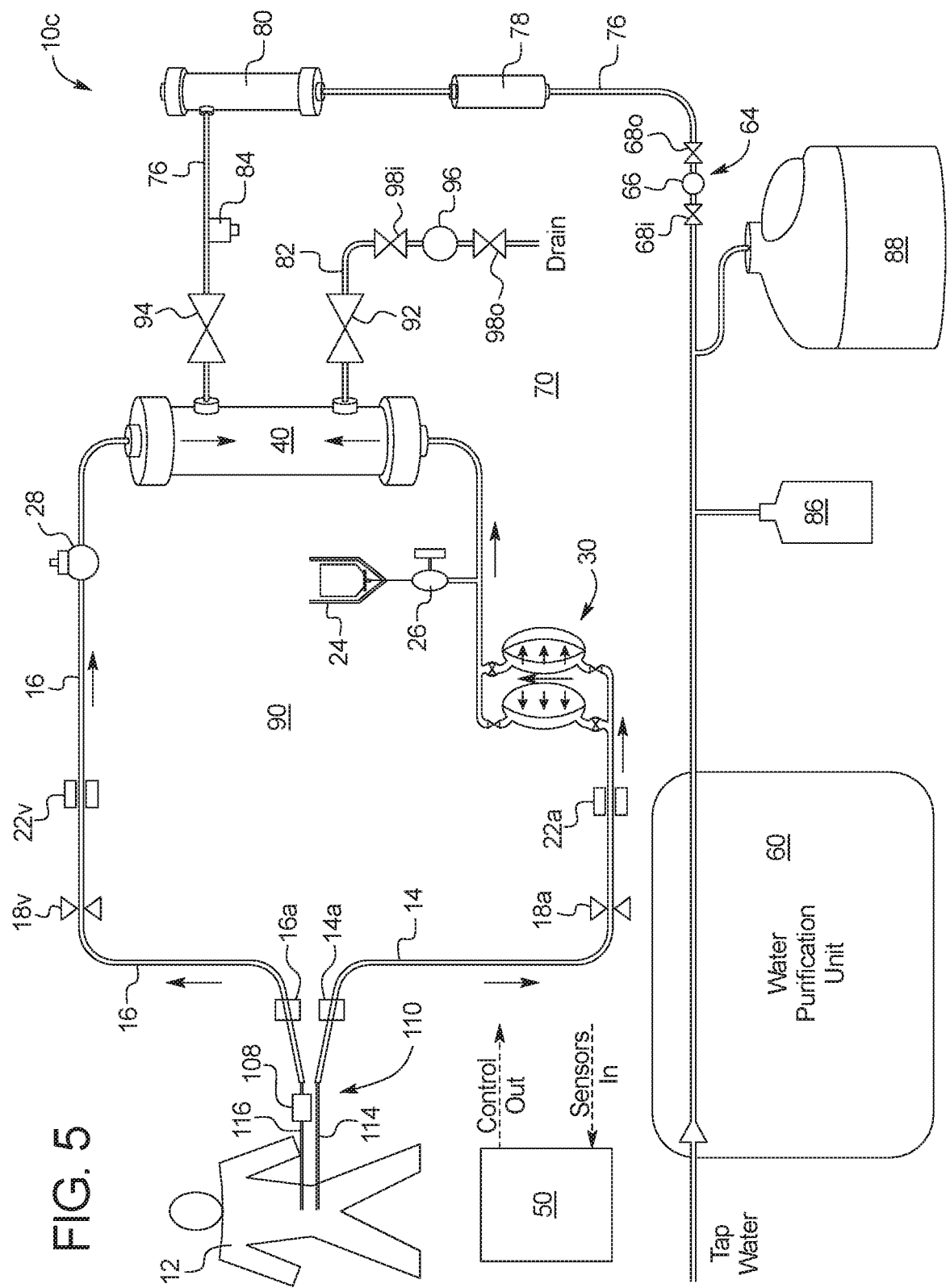
FIG. 5 is a schematic view of the CFPD system of FIG. 4 in a draining mode.

It should be appreciated that PD system 10*b* is a batch PD system in which PD fluid is pumped to patient 12, dwells within the patient and is then removed from the patient to drain. Batch PD system 10*b* can attempt to drain all the PD fluid in the drain cycle or only a portion of the PD fluid in what is known as tidal flow PD. Referring now to FIGS. 4 and 5, hemodialysis system 10*a* of FIG. 1 is used instead in any desired alternating treatment sequence with a continuous flow peritoneal dialysis ("CFPD") system 10*c*. CFPD system 10*c* is structurally very similar to that of batch PD system 10*b*, so like element numbers, including all structure, function and alternatives discussed above in FIGS. 2 and 3, are repeated and are included in FIGS. 4 and 5.

For the combination of systems 10*a* and 10*c*, hemodialysis takes place just like above with FIG. 1. Hemodialysis system 10*a* is hot water disinfected after treatment, and if a next treatment is scheduled or selected to be a PD treatment, chemical disinfectant from source 86 can be used to additionally sterilize circuits 70 and 90. Chemical disinfectant from source 86 is metered into purified water from unit 60 in the same manner described above for FIG. 2.

For CFPD system 10*c*, batch PD connection set 100 of system 10*b* is replaced with a CFPD connection set 110. CFPD connection set 110 uses dual lumens 114 and 116 instead of the "Y" or "T" connector 102, 104, 106 of batch PD connection set 100. Arterial lumen 114 is connected removably to arterial line connector 14*a* of arterial line 14, while venous lumen 116 is connected removably to venous line connector 16*a* of venous line 16, via the last chance, single use filter 108 in the illustrated embodiments. Filter 108 can again be a final ultrafilter to remove any remaining bugs or contaminants from the PD dialysate before entering the peritoneum of patient 12.

In an embodiment, CFPD system 10c is primed just as described above in connection with FIG. 2, wherein arterial line connector 14a is connected to venous line connector 16a, while CFPD connection set 110 still resides within its sterile package. Control unit 50 causes PD dialysate to be pumped via blood pump 30 and/or to-dialyzer pump 64 until all air is purged from PD patient circuit 90 and pumped to drain. At that point, arterial line connector 14a and venous line connector 16a are disconnected from each other, CFPD connection set 110 is removed from its package, connected to connectors 14a and 16a, and purged, e.g., by setting the patient-side tips of lumens at a vertical elevation that allows gravity to fill and prime CFPD connection set 110. Once primed, CFPD connection set 110 is connected to the patient's PD transfer set, which can include dual indwelling catheters, for example, one that introduces PD solution at a lower end of the patient's peritoneum, and another that removes PD solution from an upper end of the patient's peritoneum.

When prime is complete and patient 12 is connected to system 10c, control unit 50 causes the CFPD circulation illustrated in FIG. 4 to take place. CFPD does not have fills, dwells and drains as with batch PD. Instead, CFPD acts much like hemodialysis, except that blood circuit 20 is replaced with PD patient circuit 90. Fresh dialysate pump 64 and spent dialysate pump 96 pump PD dialysate with valves 92 and 94 open through the dialysate circuit 70 and dialyzer 40, cleaning the dialysate circulating through PD patient circuit 90 and pumping used dialysate to drain via drain line 82.

At the same time, control unit 50 causes blood pump 30 to circulate PD dialysate around PD patient circuit 90, into patient 12 via venous line 16 and last chance filter 108, across the peritoneum of patient 12, out arterial line 14, and back into blood pump 30. Circulation through dual loops 70 and 90 is continued for a doctor-prescribed amount of time. Online PD dialysate is prepared as needed using purified water from unit 60 and concentrate from container 88 as described above. CFPD typically requires a larger amount of PD dialysate than does batch PD.

As with batch PD system 10b, CFPD system 10c can be used with bagged dialysate, for example, if it is desired to conserve PD dialysate usage. Here, once PD patient circuit 90 is primed and patient 12 is connected to the PD patient circuit, control unit 50 instead causes blood pump 30 to circulate dialysate around PD patient circuit 90 as before, but now causes dialysate circuit valves 92 and 94 to be closed and dialysate circuit pumps 64 and 96 to remain idle. From time to time, control unit 50 can cause dialysate circuit valves 92 and 94 to be opened and dialysate circuit pumps 64 and 96 to be operated to replace a portion of PD dialysate in circuit 90, which has been running through the patient's peritoneum for some time, with new and fresh dialysate from dialysate circuit 70. This is more of a convective exchange of used dialysate with fresh dialysate as opposed to the osmotic cleaning performed when blood pump 30 and dialysate circuit pumps 64 and 96 are operated continuously.

In any case, after CFPD has been performed for the prescribed time or until a prescribed PD fluid volume has been consumed, CFPD system is drained as illustrated in FIG. 5. Here, control unit 50 causes fill valve 94 to be closed and drain valve 92 to be opened. One or both of blood pump 30 and spent dialysate pump 96 are operated to pull used dialysate through one or both of arterial line 14 and venous line 16 for a number of strokes prescribed to remove both a fill volume plus an expected amount of UF from the patient's peritoneum. Control unit 50 can again count known volume strokes of blood pump 30 and/or spent dialysate pump 96 to arrive at the prescribed removal volume. Also, as discussed above with FIGS. 1 to 3, if PD treatments are performed back to back, and patient 12 in the second PD treatment arrives at treatment full of spent PD as is often the case, the second treatment can, after prime and patient connection have been completed, begin with a drain sequence controlled by control unit 50 in the manner just described.

HD and Simplified Batch PD

Figure 6:
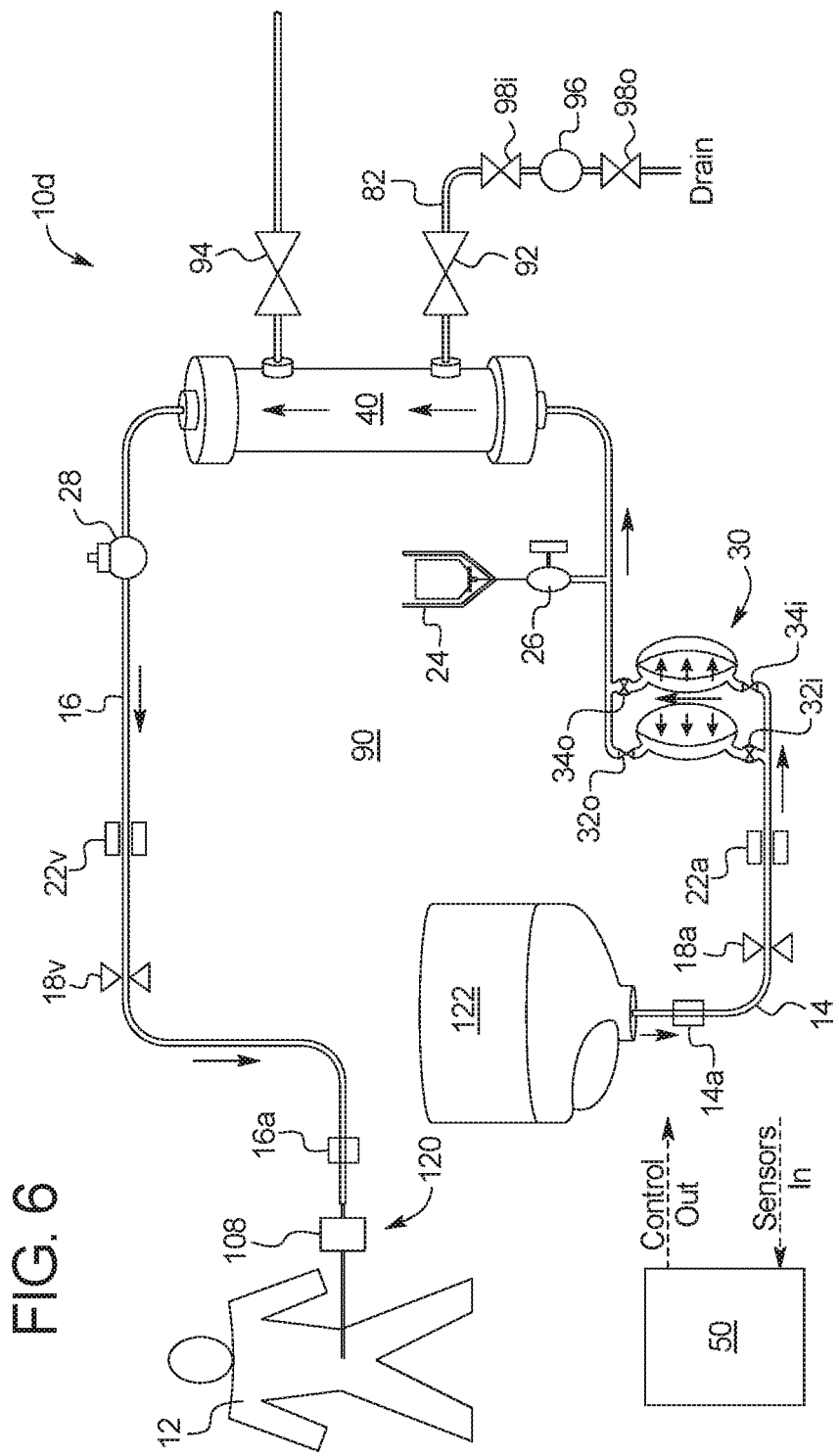
FIG. 6 is a schematic view of one embodiment of a container sourced batch PD system in a filling mode, which can be used to perform an alternative therapy to the therapy of HD system of FIG. 1.
Figure 7:
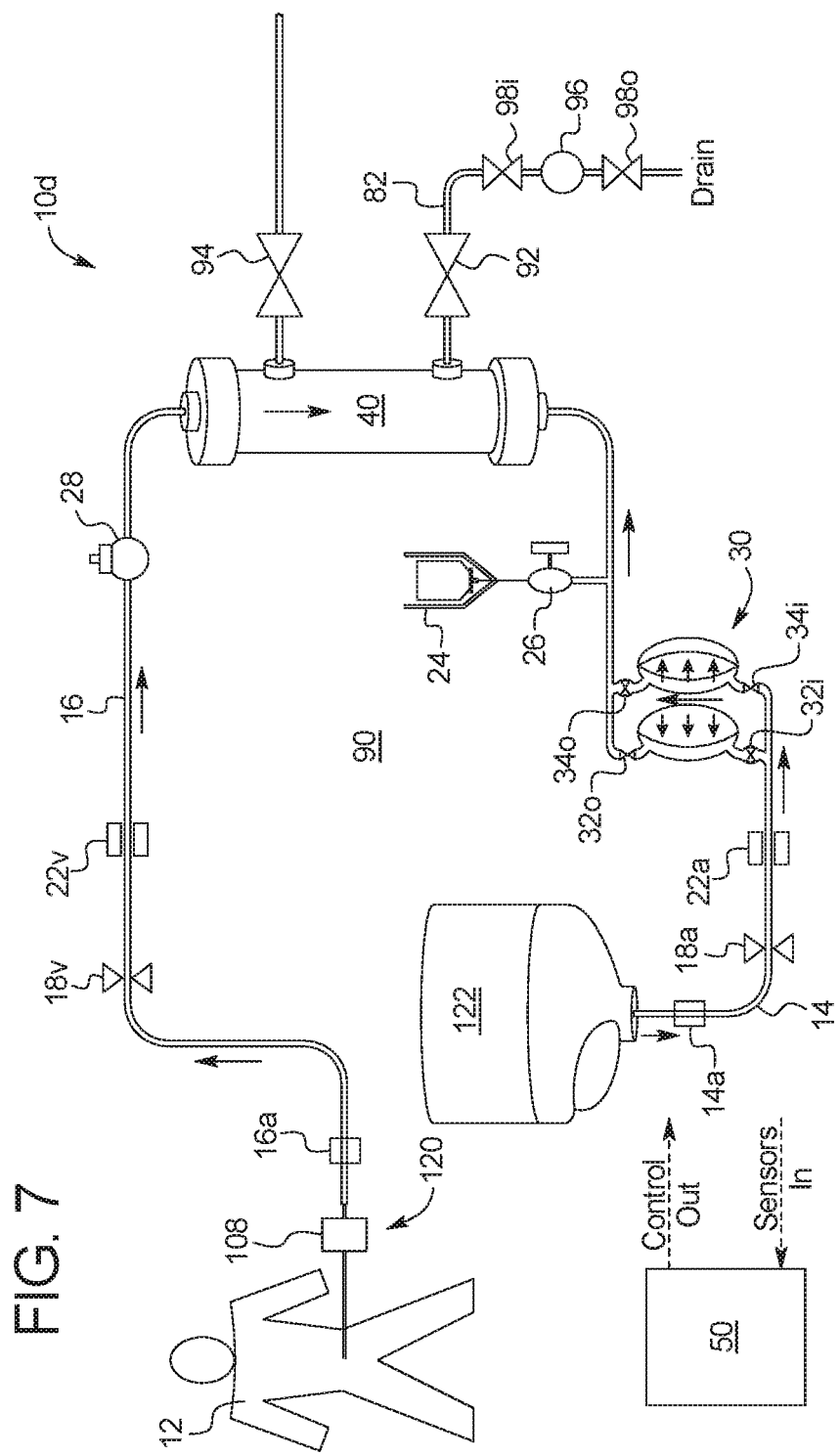
FIG. 7 is a schematic view of the container sourced batch PD system of FIG. 6.

Referring now to FIGS. 6 and 7, hemodialysis system 10a of FIG. 1 is used instead in any desired alternating treatment sequence with a simplified batch peritoneal dialysis system 10d. System 10d is structurally similar to that of batch PD system 10b and CFPD system 10c, so like element numbers, including all structure, function and alternatives discussed above in FIGS. 2 to 5, are repeated and are included in FIGS. 6 and 7.

For combination systems 10a and 10d, hemodialysis takes place just like above with FIG. 1. Hemodialysis system 10a is hot water disinfected after treatment, and if a next treatment is scheduled or selected to be a PD treatment, chemical disinfectant from source 86 can be used to additionally sterilize circuits 70 and 90. Chemical disinfectant from source 86 is metered into purified water from unit 60 in the same manner described above for FIG. 2.

For batch system 10d, batch PD connection set 100 of system 10b is replaced with a single line connection set 120. Single line connection set 120 uses a single line and single lumen instead of the "Y" or "T" connector 102, 104, 106 of batch PD connection set 100 or the dual lumens of CFPD set 110. Single line connection set 120 is connected removably via last chance, single use filter 108 to venous line connector 16a of venous line 16. Filter 108 can again be a final ultrafilter to remove any remaining bugs or contaminants from the PD dialysate before entering the peritoneum of patient 12. Also different from above, a source 122 of premade and sterilized PD dialysate is connected removably to arterial line connector 14a of venous line 14.

In an embodiment, simplified batch system 10d is primed by pumping PD dialysate from source 122 via blood pump 30, through arterial line 14, dialyzer 40, venous line 16, and to an end of single line connection set 120. The end of single line connection set 120 (as well as the ends of sets 100 and 110) can be found either by providing a hydrophobic membrane at a removable tip of connection set 120 and sensing a pressure increase at blood pump 30 once the PD dialysate hits the hydrophobic tip. Or, the end of the single line connection set 120 (or sets 100 and 110) can be set at the same elevation as source 122 (or some other pressure head source for sets 100 and 110), so that PD dialysate that is gravity fed by opening all valves 32i, 32o, 34i and 34o of blood pump 30 comes to rest naturally at the end of single line connection set 120.

When prime is complete and patient 12 is connected to system 10d as illustrated in FIG. 6, control unit 50 causes the batch filling to take place via known pump stroke volume blood pump 30. Here, dialysate valves 92 and 94 are closed, so that PD dialysate is forced through dialyzer 40, through venous line 16, and into the peritoneum of patient 12. The fill volume is measured by counting and adding the known volume pump strokes.

Once the patient's peritoneum is filled to a prescribed fill volume, control unit 50 stops blood pump 30. The PD dialysate is then allowed to reside or dwell within the patient's peritoneum for a prescribed amount of time. Batch system 10d, like system 10b, performs multiple fills, dwells and drains. System 10d, like batch system 10b, can perform total drains including expected UF, or perform partial drains and fills in a tidal peritoneal dialysis modality.

In FIG. 7, control unit 50 causes the batch draining to take place. Here, fresh dialysate fluid valve 94 is closed, while spent dialysate valve 92 is opened to allow spent dialysate to flow through drain line 82 to a house drain or drain container. In one embodiment, from-dialyzer pump 96 is used to pull a prescribed amount of drain fluid, e.g., via control unit 50 counting known volume strokes of pump 96, and push the drain fluid to drain.

Control unit 50 then repeats the above-described fill, dwell and drain process. As before, if patient 12 uses system 10d to perform peritoneal dialysis for multiple treatments in a row, the patient may have a full peritoneum from the prior PD treatment when first connecting to PD patient circuit 90. If so, patient 12 can inform control unit 50 of same. Or, control unit 50 may already know that patient 12 needs to be drained and instructs the patient to do so accordingly. In this case, control unit 50 performs an initial drain through primed PD patient circuit 90 first before performing a first fill. In an alternative embodiment, patient 12 performs a manual drain and enters the drain weight into control unit 50 before connecting to PD patient circuit 90.

In an alternative draining embodiment, and assuming PD dialysate source 122 holds a single fill volume such that the source is emptied in the fill phase of FIG. 6, control unit 50 can instead cause blood pump 30 to pump from patient 12 back to source 122. Here, dialysate valves 92 and 94 are closed, so that PD dialysate is forced through venous line 16, through dialyzer 40, through arterial line 14, and back into PD dialysate source 122. Dialysate source 122 in this embodiment is sized to hold an additional amount of UF removed from the patient during the drain phase.

Pumping Pressures for HD Versus PD

HD typically pumps at higher pressures than does PD. HD blood pumping pressures can in arterial line 14 before blood pump 30 pump be from about −50 mmHg to −300 mmHg. Arterial needle or catheter 14b restricts the inlet to blood pump 30 and creates a slight vacuum. At pressures below −250 mmHg, HD system 10a may alarm for low blood flow. The highest pressure in blood circuit 20 occurs just after blood pump 30. Post blood pump pressure is dependent on blood flow rate, dialyzer 40 pressure drop, hematocrit (percentage of red blood cells to whole blood, which determines blood viscosity), needle size for needles 14b, 16b size, and any clotting in venous blood return line 16. Blood pump pressure can be 100 to 200 mmHg higher than the pressure in venous line 16, which can for example be 100 to 250 mmHg. The venous pressure will increase if venous needle 16b is pushed against the wall of the access. It is contemplated for system 10a to monitor venous blood pressure from 0 to 500 mmHg.

The pressures in the dialysate circuit 70 are dependent on dialyzer type, ultrafiltration rate and the extracorporeal blood pressures. Typical pressure monitoring range is from −500 mmHg to +600 mmHg. Dialysate pressure can be different depending upon whether the pressure is measured at the dialyzer inlet or outlet due to the pressure drop on the dialysate side of dialyzer 40. The ultrafiltration coefficient of dialyzer 14 is also variable in the dialysate pressure. The ultrafiltration coefficient is the number of milliliters of fluid removed per hour per mmHg. It is contemplated that dialysate remain positive as much as possible to prevent the pulling of air from the dialysate solution.

Figure 10:
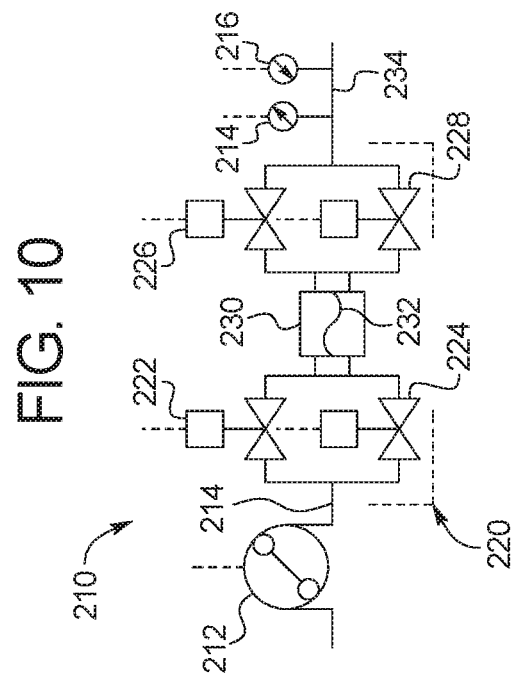
FIG. 10 is a schematic view of an alternative electrically driven system of the present disclosure, which can supply the different operating pressures required for HD versus PD.
Figure 8:
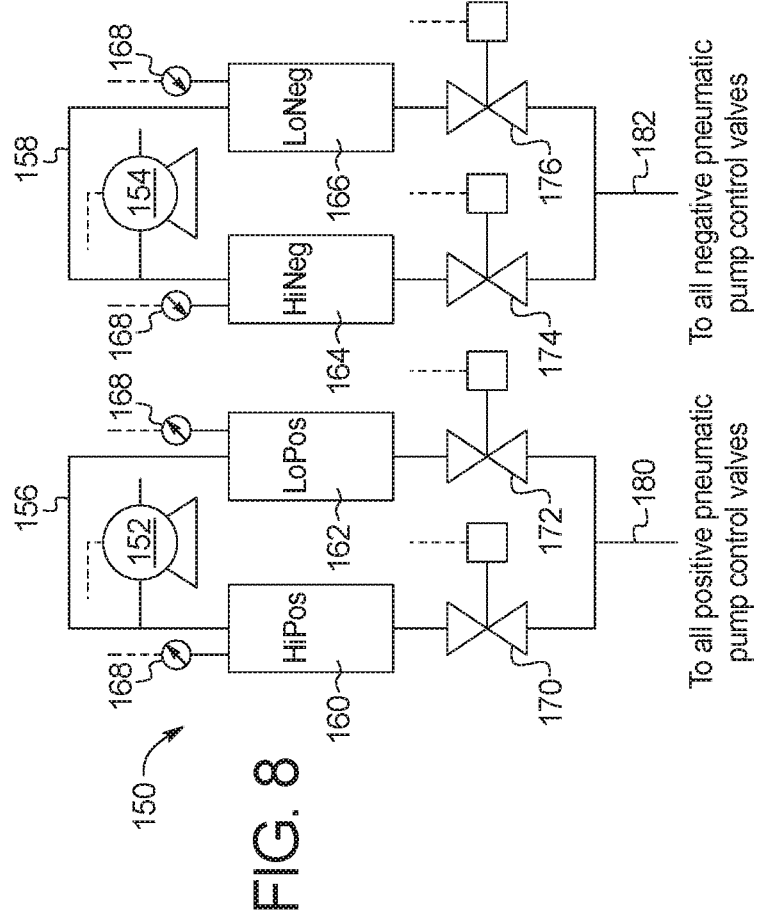
FIG. 8 is a schematic view of one embodiment of a pneumatic configuration that can be used with any of the combinations of systems discussed herein to provide the different operating pressures required for HD versus PD.
Figure 9:
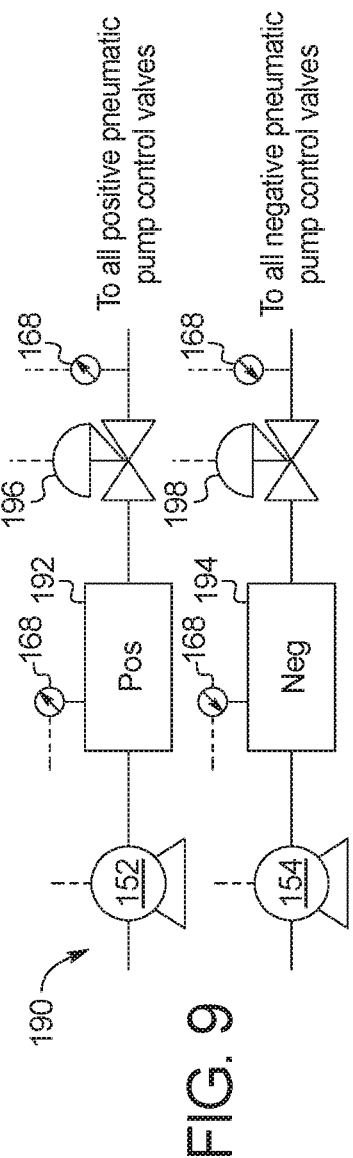
FIG. 9 is another embodiment of a pneumatic configuration that can be used with any of the combinations of systems discussed herein to provide the different operating pressures required for HD versus PD.

PD dialysate pumping pressures are less and can be, for example, up to three psig positive pumping pressure and as low as −1.5 psig negative pumping pressure. Or, PD dialysate pumping pressures can be about 78 mmHG for filling and draining. Pumping to and from the patient's peritoneum must be done at lower pressures to prevent patient discomfort and potential patient harm. HD pressures are higher due to the flowrates involved and having to push and pull blood through one or more needle. It is therefore necessary that each combination of systems 10a/10b, 10a/10c and 10a/10d be able to provide the desired operating pressures for both HD and PD. FIGS. 8 to 10 provide different alternatives for achieving different pump pressures for the different treatments. The alternatives for FIGS. 8 to 10 apply to each combination of systems 10a/10b, 10a/10c and 10a/10d.

Referring now to FIG. 8, system combinations 10a/10b, 10a/10c and 10a/10d can each employ a pneumatic pressurization system 150. Pressurization system 150 supplies the positive and negative air pressure to each of the pumps and possibly to each of the valves of system combinations 10a/10b, 10a/10c and 10a/10d. Pressurization system 150 is under control of control unit 50 of each of system combinations 10a/10b, 10a/10c and 10a/10d, and each dashed line in FIG. 8 corresponds to a data or electrical connection with control unit 50.

Pressurization system 150 includes a positive air compressor 152 and a negative air compressor 154. Positive air compressor 152 is in pneumatic communication via pneumatic line 156 with a HiPos air supply tank 160 and a LoPos air supply tank 162. Negative air compressor 154 is in pneumatic communication via pneumatic line 158 with a HiNeg air supply tank 164 and a LoNeg air supply tank 166. Positive air compressor 152 pressurizes HiPos air supply tank 160 to the highest positive pressure needed for HD dialysate and blood pumping. Positive air compressor 152 pressurizes LoPos air supply tank 162 to the highest positive pressure needed for PD dialysate pumping. Negative air compressor 154 evacuates HiNeg air supply tank 164 to the highest negative pressure needed for HD dialysate and blood pumping. Negative air compressor 154 evacuates LoNeg air supply tank 166 to the highest negative pressure needed for PD dialysate pumping. Each of the four pressures is achieved in the respective tanks through feedback to control unit 50 via an electronic pressure gauge 168, wherein compressors 152 and 154 are operated until the corresponding pressure gauge 168 indicates that the desired positive or negative pressure resides in the respective tank.

Pressurization system 150 includes electrically controlled solenoid valves 170, 172, 174 and 176 that control unit 50 opens and closes to allow HD pressure (HiPos, HiNeg) or PD pressure (LoPos, LoNeg) to be used as needed. If valve 170 is opened, HiPos air is communicated via outlet line 180 with each of a plurality of pneumatic pump control valves, which are in turn controlled via control unit 50 to selectively close the pump membranes of pumps 30, 64 and 96 for HD. If valve 172 is opened, LoPos air is communicated instead via outlet line 180 with each of the pneumatic pump control valves, which are in turn controlled via control unit 50 to selectively close the pump membranes of pumps 30, 64 and 96 for PD. If valve 174 is opened, HiNeg air is communicated via outlet line 182 with each of the pneumatic pump control valves, which are in turn controlled via control unit 50 to selectively open the pump membranes of pumps 30, 64 and 96 for HD. If valve 176 is opened, LoPos air is communicated instead via outlet line 182 with each of the pneumatic pump control valves, which are in turn controlled via control unit 50 to selectively open the pump membranes of pumps 30, 64 and 96 for PD.

In an alternative version of FIG. 8, for example if the HD and PD therapies each require different positive and negative pressures for different purposes, e.g., pump membrane versus valve membrane or dialysate pumping versus blood pumping, each of tanks 160, 162, 164 and 166 can be set on a given day for an HD treatment or a PD treatment. Thus both HiPos and LoPos tanks 160 and 162 could be set on a given day for HD or PD, while both HiNeg and LoNeg tanks 164 and 166 are correspondingly set on the given day for HD or PD. In this alternative version, separate outlet lines 180 are provided for each of HiPos and LoPos tanks 160 and 162, while separate outlet lines 182 are provided for each of HiNeg and LoNeg tanks 164 and 166. Separate outlet lines allow for simultaneous use of different positive and negative pressures.

Referring now to FIG. 9, system combinations 10a/10b, 10a/10c and 10a/10d can each alternatively employ a pneumatic pressurization system 190. Pressurization system 190 supplies the positive or negative air pressure to each of the pumps and possibly to each of the valves of system combinations 10a/10b, 10a/10c and 10a/10d. Pressurization system 190 is likewise under control of control unit 50 of each of system combinations 10a/10b, 10a/10c and 10a/10d, and each dashed line in FIG. 9 corresponds to a data or electrical connection with control unit 50.

Pressurization system 190 likewise includes a positive air compressor 152 and a negative air compressor 154. Positive air compressor 152 is in pneumatic communication with a Pos air supply tank 192. Negative air compressor 154 is in pneumatic communication with a Neg air supply tank 194. Positive air compressor 152 pressurizes Pos air supply tank 192 to the highest positive pressure needed that day for either for HD blood pumping, HD dialysate pumping or PD dialysate pumping. Negative air compressor 194 evacuates Neg air supply tank 194 to the highest negative pressure needed that day for HD dialysate or blood pumping or PD dialysate pumping. Each of tank pressure is again achieved through feedback to control unit 50 via an electronic pressure gauge 168, wherein compressors 152 and 154 are operated until the corresponding pressure gauge 168 indicates that the desired positive or negative pressure resides in the respective tank 192 or 194.

An electrically controlled positive pressure air regulator 196 is provided to regulate down the pressure of the air received from positive tank 192 if needed. Thus if tank 192 is pressurized to the positive pressure needed for HD pumping, control unit 50 could electrically control positive pressure air regulator 196 to limit the pressure to the level needed for PD dialysate pumping. Or, control unit 50 could electrically control positive pressure air regulator 196 to limit the pressure to the level needed for an HD pump or valve purpose needing less positive pressure than which resides in tank 192. Likewise, if Neg air tank 194 is pressurized to the negative pressure needed for HD pumping, control unit 50 could electrically control negative air regulator 198 to limit the negative pressure to the level needed for PD dialysate pumping. Or, control unit 50 could electrically control negative air regulator 198 to limit the pressure to the level needed for an HD pump or valve purpose needing less positive pressure than which resides in tank 194.

Downstream pressure gauges 168 are used to provide feedback to control unit 50, so that control unit 50 can servo air regulators 196 and 198 to achieve the desired pump or valve positive or negative operating pressure. While a single positive pressure air regulator 196 is illustrated operating with positive tank 192, multiple positive pressure air regulators 196 can be provided alternatively for different, simultaneous positive air pressure pumping or valve actuation. Likewise, while a single negative pressure air regulator 198 is illustrated operating with negative tank 194, multiple negative pressure air regulators 198 can be provided alternatively for different, simultaneous negative air pressure pumping or valve actuation.

Up until now, the focus of this application has been on the use of pneumatic pumps and valves. In an alternative embodiment illustrated in connection with FIG. 10, any or more or all of pumps 30, 64 and 96 of system combinations 10a/10b, 10a/10c and 10a/10d can alternatively be an electrically driven pump, such as a peristaltic tubing pump 212. Control unit 50 causes a roller of peristaltic tubing pump 212 to rotate clockwise in FIG. 10 to push fluid (blood or dialysate) under positive to a destination, such as patient 12 or dialyzer 40. Control unit 50 causes the roller of peristaltic tubing pump 212 to rotate counterclockwise in FIG. 10 to pull fluid (blood or dialysate) under negative pressure through line 214 from a source, such as patient 12 or dialyzer 40.

Control unit 50 sets the positive and negative pumping pressures by changing the speed of the rotation of the roller of pump 212. Downstream electronic pressure gauges 214 and 216 provide positive and negative pressure feedback, respectively, to control unit 50. Control unit 50 uses the pressure signal feedback to set the speed of roller pump 212 to achieve a desired positive or negative pressure at pressure gauges 214 and 216.

Also until now, volumetric control of the blood and dialysate pumps has been performed by counting and adding known volume pump strokes. It is contemplated to use other forms of volumetric control. First, any of system combinations 10a/10b, 10a/10c and 10a/10d can rely alternatively on the use of balance chambers to control dialysate or blood flow volume. Balance chambers are disclosed in the referenced publications. FIG. 10 illustrates is similar type of metering system 220 used with peristaltic pump 212. Metering system 220 includes two inlet valves 222 and 224 under control of control unit 50, two outlet valves 226 and 228 under control of control unit 50, and a central known volume pod 230 having a diaphragm 232 that flaps back and forth within pod 230, similar to the diaphragms or membranes located within pumps 30, 64 and 96.

Control unit 50 opens and closes valves 222 and 228 at the same time, and opens and closes valves 224 and 226 at the same time. Opening valve 222 allows fluid pressure to cause diaphragm 232 to move and expel a known volume of fluid through valve 228 to outlet line 234. Opening valve 224 allows fluid pressure to cause diaphragm 232 to move and expel a known volume of fluid through valve 226 to outlet line 234. Fluid flow can take place alternatively under negative pressure from line 234, through metering system 220, to pump 212. By metering flow in such a way, control unit 50 knows how much fluid that roller pump 212 is pumping by counting how many times valves 222 to 228 are sequenced. Thus, peristaltic pump 212 is not relied upon for pumping accuracy, but is, as discussed above controlled to achieve a desired positive or negative pressure at line 234.

While pneumatic valves could be used with electrically controlled peristaltic pump 212, it is also contemplated to eliminate the pneumatics altogether from any of the system combinations above. Here instead, electrically activated pinch or solenoid clamps or valves under the control of control unit 50, such as for valves 222, 224, 226 and 228, can be used.

Other forms of blood and dialysate flow volume control may be used alternatively or in addition to one or more of the above-described volume control methods. For example, one or more weigh scale in communication with control unit 50 may be used. In another example, a volume calculation using the ideal gas equation may be used. One such system and method is described in U.S. Pat. No. 8,197,439, entitled, "Fluid Volume Determination For Medical Treatment System", the entire contents of which are incorporated herein by reference and relied upon.

Additional Aspects of the Present Disclosure

Aspects of the subject matter described herein may be useful alone or in combination with any one or more of the other aspect described herein. Without limiting the foregoing description, in a first aspect of the present disclosure a dialysis system includes: a dialysis fluid pump receptacle actuated by a dialysis fluid pump actuator; a dialysis fluid line; a blood filter in fluid communication with the dialysis fluid pump receptacle via the dialysis fluid line; an extracorporeal circuit connectable to a patient; a blood pump receptacle actuated by a blood pump actuator, the blood pump receptacle in fluid communication with the blood filter via the extracorporeal circuit; and a control unit programmed to (i) in a first treatment pump peritoneal dialysis fluid through the dialysis fluid pump receptacle, the dialysis fluid line, the blood filter, the extracorporeal circuit and the blood pump receptacle to the patient's peritoneum by operating at least one of the dialysis fluid pump actuator and the blood pump actuator at a first pressure, and (ii) in a second treatment pump blood through the extracorporeal circuit, the blood pump receptacle and the blood filter to the patient by operating the blood pump actuator at a second, different pressure.

In accordance with a second aspect of the present disclosure, which may be used in combination with any other aspect or combination of aspects listed herein, the second pressure is greater than the first pressure.

In accordance with a third aspect of the present disclosure, which may be used in combination with any other aspect or combination of aspects listed herein, at least one of the dialysis fluid pump receptacle and the blood pump receptacle includes a chamber housing a moveable diaphragm.

In accordance with a fourth aspect of the present disclosure, which may be used in combination with any other aspect or combination of aspects listed herein, at least one of the dialysis fluid pump receptacle and the blood pump receptacle includes a tube section.

In accordance with a fifth aspect of the present disclosure, which may be used in combination with any other aspect or combination of aspects listed herein, the control unit in the second treatment is further programmed to pump hemodialysis fluid through the dialysis fluid pump receptacle, the dialysis fluid line and the blood filter by operating the dialysis fluid pump actuator at a pressure different than the first pressure.

In accordance with a sixth aspect of the present disclosure, which may be used in combination with any other aspect or combination of aspects listed herein, the control unit in the first treatment operates the dialysis fluid pump actuator and the blood pump actuator at the same first pressure.

In accordance with a seventh aspect of the present disclosure, which may be used in combination with any other aspect or combination of aspects listed herein, the dialysis fluid pump receptacle is a first dialysis fluid pump receptacle, the dialysis fluid pump actuator is a first dialysis fluid pump actuator, and the dialysis fluid line is a first dialysis fluid line, and which includes a second dialysis fluid pump receptacle, a second dialysis fluid pump actuator, and a second dialysis fluid line, the blood filter in fluid communication with the second dialysis fluid pump receptacle via the second dialysis fluid line; and wherein the control unit is configured to cause the second dialysis fluid pump actuator to pump used peritoneal dialysis fluid or used hemodialysis fluid from the filter and through the second dialysis fluid line.

In accordance with an eighth aspect of the present disclosure, which may be used in combination with the seventh aspect and any other aspect or combination of aspects listed herein, in the first treatment, the second dialysis fluid pump actuator pumps used peritoneal dialysis fluid in two directions through the through the extracorporeal circuit to the blood filter.

In accordance with a ninth aspect of the present disclosure, which may be used in combination with the eighth aspect and any other aspect or combination of aspects listed herein, one of the directions through the extracorporeal includes the blood pump receptacle, and wherein used peritoneal dialysis fluid flow in that direction is aided by the blood pump actuator.

In accordance with a tenth aspect of the present disclosure, which may be used in combination with any other aspect or combination of aspects listed herein, in the first treatment, the first dialysis fluid pump actuator pumps fresh peritoneal dialysis fluid through the blood filter and in two directions through the extracorporeal circuit to the patient's peritoneum.

In accordance with an eleventh aspect of the present disclosure, which may be used in combination with the tenth aspect and any other aspect or combination of aspects listed herein, one of the directions through the extracorporeal includes the blood pump receptacle, and wherein fresh peritoneal dialysis fluid flow in that direction is aided by the blood pump actuator.

In accordance with a twelfth aspect of the present disclosure, which may be used in combination with any other aspect or combination of aspects listed herein, a dialysis system includes: a dialysis fluid pump receptacle actuated by a dialysis fluid pump actuator; a dialysis fluid line; a blood filter in fluid communication with the dialysis fluid pump receptacle via the dialysis fluid line; an extracorporeal circuit connectable to a patient; a blood pump receptacle actuated by a blood pump actuator, the blood pump receptacle in fluid communication with the blood filter via the extracorporeal circuit; and a control unit programmed to (i) in a first treatment create peritoneal dialysis fluid by combining purified water with a peritoneal dialysis concentrate, and (ii) in a second treatment create hemodialysis fluid by combining purified water with a hemodialysis concentrate.

In accordance with a thirteenth aspect of the present disclosure, which may be used in combination with the twelfth aspect and any other aspect or combination of aspects listed herein, the dialysis system includes a plurality of conductivity sensors in operable communication with the control unit and the hemodialysis fluid as the fluid is combined for controlling the combining purified water with the hemodialysis concentrate.

In accordance with a fourteenth aspect of the present disclosure, which may be used in combination with the twelfth aspect and any other aspect or combination of aspects listed herein, the dialysis system includes at least one proportioning pump for pumping the purified water and the peritoneal dialysis concentrate, the at least one proportioning pump in operable communication with the control unit for controlling the combining of the peritoneal dialysis fluid.

In accordance with a fifteenth aspect of the present disclosure, which may be used in combination with any other aspect or combination of aspects listed herein, a dialysis system includes: a first dialysis fluid pump receptacle actuated by a first dialysis fluid pump actuator; a first dialysis fluid line; a second dialysis fluid pump receptacle actuated by a second dialysis fluid pump actuator; a second dialysis fluid line; a blood filter in fluid communication with the first dialysis fluid pump receptacle via the first dialysis fluid line and the second dialysis fluid pump receptacle via the second dialysis fluid line; an extracorporeal circuit connectable to a patient; a blood pump receptacle actuated by a blood pump actuator, the blood pump receptacle in fluid communication with the blood filter via the extracorporeal circuit; and a control unit programmed to (i) in a first treatment pump peritoneal dialysis fluid in a continuous flow manner through the first dialysis fluid pump receptacle, the first dialysis fluid line, the blood filter, the extracorporeal circuit, the blood pump receptacle, the patient's peritoneum, back through the blood filter, the second dialysis fluid line, and the second dialysis fluid pump receptacle by operating at least two of the first dialysis fluid pump actuator, the second dialysis fluid pump actuator and the blood pump actuator, and (ii) in a second treatment pump blood through the extracorporeal circuit, the blood pump receptacle and the blood filter to the patient by operating the blood pump.

In accordance with a sixteenth aspect of the present disclosure, which may be used in combination with the fifteenth aspect and any other aspect or combination of aspects listed herein, the control unit in the second blood treatment is programmed to cause (i) the first dialysis fluid pump actuator to pump fresh hemodialysis fluid through the first dialysis fluid pump receptacle, the first dialysis fluid line and the blood filter and (ii) the second dialysis fluid pump actuator to pump used hemodialysis from the blood filter through the second dialysis fluid pump receptacle and the second dialysis fluid line.

In accordance with a seventeenth aspect of the present disclosure, which may be used in combination with the fifteenth aspect and any other aspect or combination of aspects listed herein, in the first treatment, the blood pump actuator pumps used peritoneal dialysis fluid through the blood pump receptacle back to the blood filter.

In accordance with an eighteenth aspect of the present disclosure, which may be used in combination with the fifteenth aspect and any other aspect or combination of aspects listed herein, in the first treatment, the first dialysis fluid pump actuator pumps fresh peritoneal dialysis fluid through the blood filter, through a portion of the extracorporeal circuit, to the patient's peritoneum.

In accordance with a nineteenth aspect of the present disclosure, which may be used in combination with any other aspect or combination of aspects listed herein, a dialysis system includes: a dialysis fluid pump receptacle actuated by a dialysis fluid pump actuator; a dialysis fluid line; a blood filter in fluid communication with the dialysis fluid pump receptacle via the dialysis fluid line; an extracorporeal circuit connectable to a patient; a blood pump receptacle actuated by a blood pump actuator, the blood pump receptacle in fluid communication with the blood filter via the extracorporeal circuit; and a control unit programmed to (i) in a first treatment pump peritoneal dialysis fluid from a source, through the extracorporeal circuit, the blood pump receptacle and the blood filter to the patient by operating the blood pump actuator, and (ii) in a second treatment pump blood through the extracorporeal circuit, the blood pump receptacle and the blood filter to the patient by operating the blood pump actuator.

In accordance with a twentieth aspect of the present disclosure, which may be used in combination with the nineteenth aspect and any other aspect or combination of aspects listed herein, in the first treatment the dialysis fluid line is occluded and in the second treatment the dialysis fluid line is open for at least part of the treatment.

In accordance with a twenty-first aspect of the present disclosure, any of the structure and functionality illustrated and described in connection with FIGS. 1 to 10 may be used in combination with any other aspect or combination of aspects listed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
    an online blood treatment fluid source and a treatment fluid pump provided at a first time, the treatment fluid pump positioned and arranged to deliver blood treatment fluid via the online blood treatment fluid source;
    at least one source of peritoneal dialysis fluid separate from the treatment fluid pump provided at a second time;
    a first fluid line;
    a second fluid line in fluid communication with the at least one source of peritoneal dialysis fluid;
    at least one pump positioned and arranged to pump blood through the first fluid line at the first time;
    a first patient connector configured to be removably placed in fluid communication with the first fluid line to allow a blood treatment to be performed at a first pressure supplied by the at least one pump at the first time; and
    a second patient connector configured to be removably placed in fluid communication with the second fluid line to allow a peritoneal dialysis treatment to be performed at a second pressure applied to peritoneal dialysis fluid delivered from the peritoneal dialysis fluid source to the second fluid line at the second time.

2. The dialysis fluid system of claim 1, wherein the first patient connector includes hemodialysis needles.

3. The dialysis fluid system of claim 1, wherein the second patient connector includes a peritoneal dialysis connection set.

4. The dialysis fluid system of claim 1, wherein the at least one pump is used additionally to pump peritoneal dialysis fluid to perform the peritoneal dialysis treatment.

5. The dialysis fluid system of claim 1, which includes a dialyzer at the first time located between the treatment fluid pump and the at least one pump positioned and arranged to pump blood.

6. The dialysis fluid system of claim 1, wherein the at least one source of peritoneal dialysis fluid is a premade source of peritoneal dialysis fluid.

7. The dialysis fluid system of claim 1, wherein the first fluid line is provided at the first time and the second fluid line is provided at the second time.

8. The dialysis fluid system of claim 1, wherein the at least one pump is a peristaltic pump.

9. The dialysis fluid system of claim 1, wherein the online blood treatment fluid source includes a water purification machine and at least one source of concentrate.

10. The dialysis fluid system of claim 9, wherein the at least one source of concentrate includes at least one of: (i) an acid container; or (ii) a bicarbonate cartridge.

11. The dialysis fluid system of claim 1, which includes a control unit programmed to pump peritoneal dialysis fluid from the at least one source of peritoneal dialysis fluid through a blood filter to perform the peritoneal dialysis treatment with the second patient connector.

12. The dialysis fluid system of claim 1, which includes a control unit programmed to drain a patient using the second connector when a peritoneal dialysis treatment is to be performed.

13. The dialysis fluid system of claim 1, wherein the online blood treatment fluid source includes a water purification machine and at least one source of concentrate.

14. A dialysis system comprising:
an online blood treatment fluid source and a treatment fluid pump provided at a first time, the treatment fluid pump positioned and arranged to deliver blood treatment fluid via the online blood treatment fluid source;
at least one source of peritoneal dialysis fluid separate from the treatment fluid pump provided at a second time;
a first fluid line;
a second fluid line in fluid communication with the at least one source of peritoneal dialysis fluid;
at least one pump positioned and arranged to pump blood through the first fluid line at the first time;
a first patient connector configured to be removably placed in fluid communication with the first fluid line to allow a blood treatment to be performed at a blood treatment pressure between −300 mmHg to 500 mmHg at the first time; and
a second patient connector configured to be removably placed in fluid communication with the second fluid line to allow a peritoneal dialysis treatment to be performed at a peritoneal dialysis pressure between −1.5 psig and 3 psig applied to peritoneal dialysis fluid delivered from the peritoneal dialysis fluid source to the second fluid line at the second time.

15. The dialysis fluid system of claim 14, wherein the at least one pump supplies the blood treatment pressure and the peritoneal dialysis pressure.

16. The dialysis fluid system of claim 15, wherein the at least one pump is a peristaltic pump.

17. The dialysis fluid system of claim 15, wherein the first fluid line is provided at the first time and the second fluid line is provided at the second time.

18. A dialysis system comprising:
an online blood treatment fluid source and a treatment fluid pump provided at a first time, the treatment fluid pump positioned and arranged to deliver blood treatment fluid via the online blood treatment fluid source;
a dialyzer provided at the first time and positioned and arranged to receive blood treatment fluid from the online blood treatment fluid source at a first pressure;
at least one source of peritoneal dialysis fluid separate from the treatment fluid pump provided at a second time; and
at least one pump positioned and arranged to pump peritoneal dialysis fluid from the at least one source of peritoneal dialysis fluid to a patient at the second time and at a second pressure.

19. The dialysis system of claim 18, wherein the peritoneal dialysis fluid is pumped through the dialyzer to the patient at the second time.

20. The dialysis system of claim 18, wherein the at least one source of peritoneal dialysis fluid is a premade source of peritoneal dialysis fluid.

21. The dialysis fluid system of claim 18, wherein the at least one pump is a peristaltic pump.

* * * * *